United States Patent
Kuvaeva et al.

(10) Patent No.: US 9,873,898 B2
(45) Date of Patent: Jan. 23, 2018

(54) METHOD FOR PRODUCING AN L-AMINO ACID USING A BACTERIUM OF THE FAMILY ENTEROBACTERIACEAE HAVING ATTENUATED EXPRESSION OF A PHOSPHATE TRANSPORTER-ENCODING GENE

(71) Applicant: AJINOMOTO CO., INC., Tokyo (JP)

(72) Inventors: Tatyana Mikhailovna Kuvaeva, Moscow (RU); Evgeniya Aleksandrovna Polyakova, Moscow (RU); Natalia Viktorovna Stoynova, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/082,274

(22) Filed: Mar. 28, 2016

(65) Prior Publication Data

US 2016/0201100 A1 Jul. 14, 2016

Related U.S. Application Data

(63) Continuation of application No. PCT/JP2014/077027, filed on Oct. 2, 2014.

(30) Foreign Application Priority Data

Oct. 2, 2013 (RU) .................... 2013144250

(51) Int. Cl.

| | |
|---|---|
| *C12P 13/24* | (2006.01) |
| *C12N 15/00* | (2006.01) |
| *C12Q 1/68* | (2006.01) |
| *C07H 21/04* | (2006.01) |
| *C07K 1/00* | (2006.01) |
| *C12P 13/06* | (2006.01) |
| *C12P 13/08* | (2006.01) |
| *C12P 13/10* | (2006.01) |
| *C12P 13/12* | (2006.01) |
| *C12P 13/14* | (2006.01) |
| *C12P 13/22* | (2006.01) |
| *C07K 14/24* | (2006.01) |
| *C12N 1/20* | (2006.01) |
| *C12P 13/04* | (2006.01) |

(52) U.S. Cl.
CPC ............. *C12P 13/24* (2013.01); *C07K 14/24* (2013.01); *C12N 1/20* (2013.01); *C12P 13/04* (2013.01); *C12P 13/06* (2013.01); *C12P 13/08* (2013.01); *C12P 13/10* (2013.01); *C12P 13/12* (2013.01); *C12P 13/14* (2013.01); *C12P 13/222* (2013.01); *C12P 13/227* (2013.01)

(58) Field of Classification Search
None
See application file for complete search history.

(56) References Cited

U.S. PATENT DOCUMENTS

| | | | |
|---|---|---|---|
| 4,278,765 A | 7/1981 | Debabov et al. | |
| 4,346,170 A | 8/1982 | Sano et al. | |
| 5,661,012 A | 8/1997 | Sano et al. | |
| 5,932,453 A | 8/1999 | Kikuchi et al. | |
| 5,965,391 A | 10/1999 | Reinscheid et al. | |
| 5,998,178 A | 12/1999 | Hashiguchi et al. | |
| 6,040,160 A | 3/2000 | Kojima et al. | |
| 8,460,903 B2 | 6/2013 | Savrasova et al. | |
| 8,679,798 B2 | 3/2014 | Yampolskaya et al. | |
| 8,852,897 B2 | 10/2014 | Savrasova et al. | |
| 9,051,591 B2 | 6/2015 | Kuvaeva et al. | |
| 9,175,319 B2 | 11/2015 | Stoynova et al. | |
| 2002/0058315 A1 | 5/2002 | Lunts et al. | |
| 2002/0106751 A1* | 8/2002 | Farwick | C07K 14/34 435/106 |
| 2006/0121558 A1 | 6/2006 | Stephanopoulos et al. | |
| 2006/0216796 A1 | 9/2006 | Hashiguchi et al. | |
| 2014/0335574 A1 | 11/2014 | Sycheva et al. | |
| 2015/0017693 A1 | 1/2015 | Sycheva et al. | |

FOREIGN PATENT DOCUMENTS

| | | |
|---|---|---|
| EP | 0685555 | 5/1995 |
| WO | WO95/16042 | 6/1995 |
| WO | WO96/15246 | 5/1996 |

OTHER PUBLICATIONS

Harris. Characterization of PitA and PitB from *Escherichia coli*. Journal of Bacteriology, Sep. 2001, p. 5008-5014.*
Branden et al. Introduction to Protein Structure, Garland Publishing Inc., New York, p. 247, 1991.*
Beard, S. J. et al., "Evidence for the transport of zinc(II) ions via the Pit inorganic phosphate transport system in *Escherichia coli*," FEMS Microbiol. Lett. 2000;184:231-235.
Harris, R. M., et al., "Characterization of PitA and PitB from *Escherichia coli*," J. Bacteriol. 2001;183(17):5008-5014.
Hoffer, S. M., et al., "Activation by Gene Amplification of pitB, Encoding a Third Phosphate Transporter of *Escherichia coli* K-12," J. Bacteriol. 2001;183(15):4659-4663.
Martinez, P., et al., "Physiological Regulation of the Derepressible Phosphate Transporter in *Saccharomyces cerevisiae*," J. Bacteriol. 1998;180(8):2253-2256.
Van Veen, H. W., et al., "Mechanism and Energetics of the Secondary Phosphate Transport System of Acinetobacter johnsonii 210A," J. Biol. Chem. 1993;268(26):19377-19383.
Van Veen, H. W., et al., "Translocation of Metal Phosphate via the Phosphate Inorganic Transport System of *Escherichia coli*," Biochem. 1994;33:1766-1770.
Versaw, W. K., et al., "Repressible cation-phosphate symporters in Neurospora crassa," Proc. Natl. Acad. Sci. USA 1995;92:3884-3887.
International Search Report and Written Opinion for PCT Patent App. No. PCT/JP2014/077027 (dated Mar. 25, 2015).

* cited by examiner

*Primary Examiner* — Yong Pak
(74) *Attorney, Agent, or Firm* — Shelly Guest Cermak; Cermak Nakajima & McGowan LLP

(57) ABSTRACT

The present invention provides a method for producing an L-amino acid by fermentation using a bacterium of the family Enterobacteriaceae. The bacterium can belong to the genus *Escherichia*, which has been modified to attenuate expression of a phosphate transporter-encoding gene, such as the pitA gene or pitB gene.

4 Claims, 1 Drawing Sheet

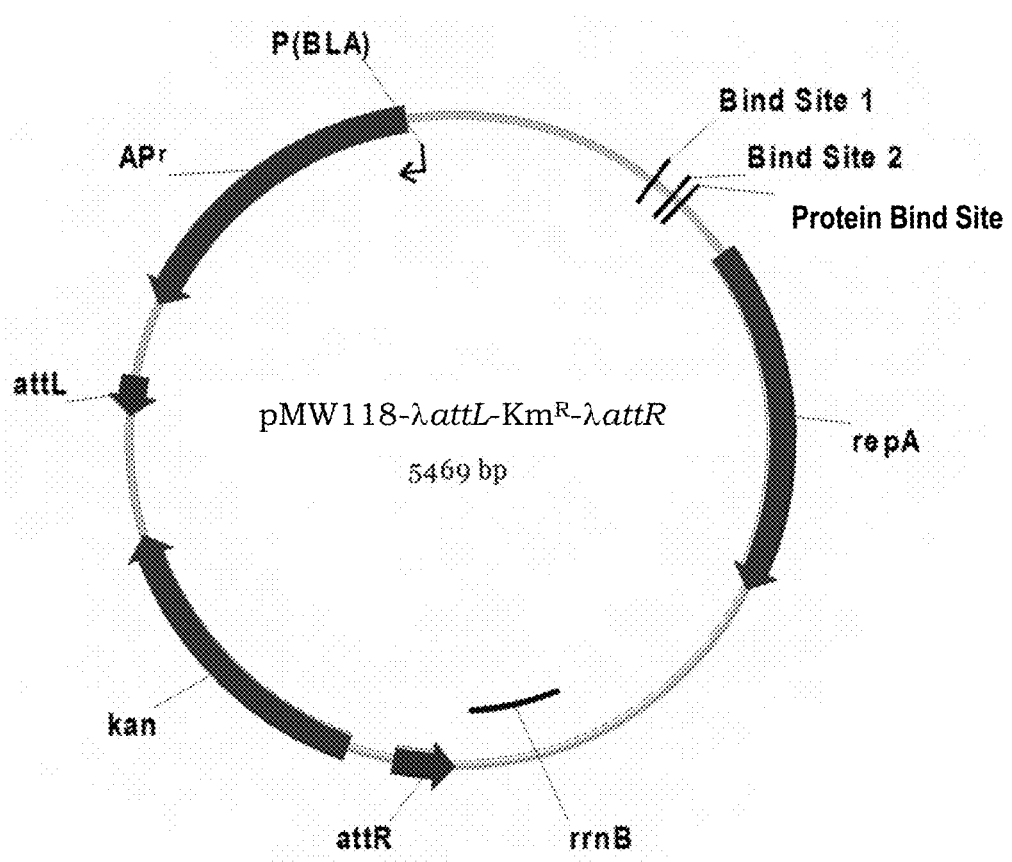

ved by the findings that attenuation

SEQUENCE LISTING

<160> NUMBER OF SEQ ID NOS: 11

<210> SEQ ID NO 1
<211> LENGTH: 1500
<212> TYPE: DNA
<213> ORGANISM: Escherichia coli

<400> SEQUENCE: 1

```
atgctacatt tgtttgctgg cctggatttg cataccgggc tgttattatt gcttgcactg        60
gcttttgtgc tgttctacga agccatcaat ggtttccatg acacagccaa cgccgtggca       120
accgttatct atacccgcgc gatgcgttct cagctcgccg tggttatggc ggcggtattc       180 aacttttttgg gtgttttgct gggtggtctg agtgttgcct atgccattgt gcatatgctg      240
ccgacggatc tgctgcttaa tatgggatcg tctcatggcc ttgccatggt gttctctatg      300
ttgctggcgg cgattatctg gaacctgggt acctggtact tggtttacc tgcatccagc       360 tctcatacgc tgattggcgc gatcatcggg attggtttaa ccaatgcgtt gatgaccggg      420
acgtcagtgg tggatgcact caatatcccg aaagtattaa gtattttcgg ttctctgatc      480 gttccccta ttgtcggcct ggtgtttgct ggcggtctga ttttcttgct gcgtcgctac       540
tggagcggca ccaagaaacg cgcccgtatc cacctgaccc cagcggagcg tgaaaagaaa      600
gacggcaaga aaaagccgcc gttctggacg cgtattgcgc tgatcctttc cgctatcggc      660
gtggcgtttt cgcacggcgc gaacgatggt cagaaaggca ttggtctggt tatgttggta      720
ttgattggcg tcgcgccagc aggcttcgtg gtgaacatga atgccactgg ctacgaaatc      780
acccgtaccc gtgatgccat caacaacgtc gaagcttact ttgagcagca tcctgcgctg      840
ctcaaacagg ctaccggtgc tgatcagtta gtaccggctc cggaagctgg cgcaacgcaa      900
cctgcggagt ccactgcca tccgtcgaat accattaacg cgctcaaccg cctgaaaggt      960
atgttgacca ccgatgtgga aagctacgac aagctgtcgc ttgatcaacg tagccagatg     1020
cgccgcatta tgctgtgcgt ttctgacact atcgacaaag tggtgaagat gcctggcgtg     1080
agtgctgacg atcagcgcct gttgaagaaa ctgaagtccg acatgcttag caccatcgag     1140
tatgcaccgg tgtggatcat catggcggtc gcgctggcgt taggtatcgg tacgatgatt     1200
ggctggcgcc gtgtggcaac gactatcggt gagaaaatcg gtaagaaagg catgacctac     1260
gctcagggga tgtctgccca tgatgacggcg gcagtgtcta tcggcctggc gagttatacc    1320
gggatgccgg tttccactac tcacgtactc tcctcttctg tcgcggggac gatggtggta     1380
gatggtggcg gcttacagcg taaaaccgtg accagcattc tgatggcctg ggtgtttacc     1440
cttccggctg cggtactgct ttccgcgggg ctgtactggc tctccttgca gttcctgtaa    1500
```

-continued

```
<210> SEQ ID NO 2
<211> LENGTH: 499
<212> TYPE: PRT
<213> ORGANISM: Escherichia coli

<400> SEQUENCE: 2

Met Leu His Leu Phe Ala Gly Leu Asp Leu His Thr Gly Leu Leu
1               5                   10                  15

Leu Leu Ala Leu Ala Phe Val Leu Phe Tyr Glu Ala Ile Asn Gly Phe
            20                  25                  30

His Asp Thr Ala Asn Ala Val Ala Thr Val Ile Tyr Thr Arg Ala Met
            35                  40                  45

Arg Ser Gln Leu Ala Val Val Met Ala Ala Val Phe Asn Phe Leu Gly
50                  55                  60

Val Leu Leu Gly Gly Leu Ser Val Ala Tyr Ala Ile Val His Met Leu
65                  70                  75                  80

Pro Thr Asp Leu Leu Leu Asn Met Gly Ser Ser His Gly Leu Ala Met
                85                  90                  95

Val Phe Ser Met Leu Leu Ala Ala Ile Ile Trp Asn Leu Gly Thr Trp
            100                 105                 110

Tyr Phe Gly Leu Pro Ala Ser Ser Ser His Thr Leu Ile Gly Ala Ile
            115                 120                 125

Ile Gly Ile Gly Leu Thr Asn Ala Leu Met Thr Gly Thr Ser Val Val
130                 135                 140

Asp Ala Leu Asn Ile Pro Lys Val Leu Ser Ile Phe Gly Ser Leu Ile
145                 150                 155                 160

Val Ser Pro Ile Val Gly Leu Val Phe Ala Gly Gly Leu Ile Phe Leu
                165                 170                 175

Leu Arg Arg Tyr Trp Ser Gly Thr Lys Lys Arg Ala Arg Ile His Leu
            180                 185                 190

Thr Pro Ala Glu Arg Glu Lys Lys Asp Gly Lys Lys Pro Pro Phe
            195                 200                 205

Trp Thr Arg Ile Ala Leu Ile Leu Ser Ala Ile Gly Val Ala Phe Ser
210                 215                 220

His Gly Ala Asn Asp Gly Gln Lys Gly Ile Gly Leu Val Met Leu Val
225                 230                 235                 240

Leu Ile Gly Val Ala Pro Ala Gly Phe Val Val Asn Met Asn Ala Thr
                245                 250                 255

Gly Tyr Glu Ile Thr Arg Thr Arg Asp Ala Ile Asn Asn Val Glu Ala
            260                 265                 270

Tyr Phe Glu Gln His Pro Ala Leu Leu Lys Gln Ala Thr Gly Ala Asp
            275                 280                 285

Gln Leu Val Pro Ala Pro Glu Ala Gly Ala Thr Gln Pro Ala Glu Phe
290                 295                 300

His Cys His Pro Ser Asn Thr Ile Asn Ala Leu Asn Arg Leu Lys Gly
305                 310                 315                 320

Met Leu Thr Thr Asp Val Glu Ser Tyr Asp Lys Leu Ser Leu Asp Gln
                325                 330                 335

Arg Ser Gln Met Arg Arg Ile Met Leu Cys Val Ser Asp Thr Ile Asp
            340                 345                 350

Lys Val Val Lys Met Pro Gly Val Ser Ala Asp Gln Arg Leu Leu
            355                 360                 365

Lys Lys Leu Lys Ser Asp Met Leu Ser Thr Ile Glu Tyr Ala Pro Val
370                 375                 380
```

```
Trp Ile Ile Met Ala Val Ala Leu Ala Leu Gly Ile Gly Thr Met Ile
385                 390                 395                 400

Gly Trp Arg Arg Val Ala Thr Thr Ile Gly Glu Lys Ile Gly Lys Lys
                405                 410                 415

Gly Met Thr Tyr Ala Gln Gly Met Ser Ala Gln Met Thr Ala Ala Val
            420                 425                 430

Ser Ile Gly Leu Ala Ser Tyr Thr Gly Met Pro Val Ser Thr Thr His
        435                 440                 445

Val Leu Ser Ser Ser Val Ala Gly Thr Met Val Val Asp Gly Gly
    450                 455                 460

Leu Gln Arg Lys Thr Val Thr Ser Ile Leu Met Ala Trp Val Phe Thr
465                 470                 475                 480

Leu Pro Ala Ala Val Leu Leu Ser Gly Gly Leu Tyr Trp Leu Ser Leu
                485                 490                 495

Gln Phe Leu

<210> SEQ ID NO 3
<211> LENGTH: 1500
<212> TYPE: DNA
<213> ORGANISM: Escherichia coli

<400> SEQUENCE: 3
atgctaaatt tatttgttgg ccttgatata tacacagggc ttttgttatt gcttgctctg      60
gcatttgtgt tgttctacga agcaatcaat ggttttcatg acacggcgaa tgcggtggca     120
gccgttattt atactcgtgc catgcaacca caacttgctg tggtgatggc ggcatttttt     180
aacttttttg gcgtgttatt gggcggactt agcgttgcct atgccattgt ccatatgttg     240
ccaaccgatt tgttgctgaa tatggggtca acccacggcc tggcgatggt cttttccatg     300
ctgctggcgg cgattatctg gaacctggga acgtggttct tcggtttacc ggcctccagt     360
tcgcacacct tgattggtgc gattatcggc atcggtttaa ccaacgcgct gttaaccggc     420
tcatcggtga tggatgcgtt aaacctgcgt gaagtgacca aaattttctc ctcgctgatt     480 gtttcccta tcgtcggcct ggtcattgcg ggaggcctga tattcctgct gcgacgctac     540
tggagcggga cgaaaaagcg tgaccgtatt caccgcattc cggaagatcg caaaaagaaa     600
aaaggcaaac gtaaaccgcc attctggacg cgtattgcgc tgattgtttc cgctgcgggc     660
gtggcgtttt cgcacggcgc gaacgacgga caaaaaggga tcggcctggt aatgctggta     720
ctggtgggga ttgcccctgc tggcttcgtc gtcaatatga atgcgtccgg ctatgaaatt     780
acccgtaccc gcgatgccgt taccaacttc gaacactacc tgcaacagca tcctgaactg     840
ccgcagaagt tgattgcgat ggaacctcca ttgcctgcag catcgactga tggcacgcaa     900
gtaacagagt ttcactgtca tccggcaaat acctttgatg ctattgcgcg cgttaaaacg     960
atgctgccag gcaatatgga aagttacgag ccgttaagcg tgagtcagcg cagccagctg    1020
cgccgcatta tgctgtgcat ctctgatacc tccgcgaagc tagcgaaact gccaggcgtc    1080
agtaaagaag accagaacct gctgaaaaaa cttcgcagcg atatgttaag caccattgag    1140
tacgctccgg tgtggatcat catggcggta gcactggcgc tcggcattgg caccatgatt    1200
ggctggcgtc gtgtagcgat gaccatcggt gagaagattg gtaagcgcgg catgacgtat    1260
gcgcaaggca tggcggcaca aatgacggcg gcagtgtcta tcggtcttgc cagttatatt    1320
gggatgcccg tctccacaac acacgtcctc tcgtctgcag ttgcagggac gatggtggtg    1380
```

```
gacggcggtg ggttacagcg taaaacggta accagcatcc tgatggcgtg ggtatttact    1440
ttaccggcgg caattttttct ttctggtggg ctgtactgga tagcattgca gttgatttaa   1500
```

<210> SEQ ID NO 4
<211> LENGTH: 499
<212> TYPE: PRT
<213> ORGANISM: Escherichia coli

<400> SEQUENCE: 4

```
Met Leu Asn Leu Phe Val Gly Leu Asp Ile Tyr Thr Gly Leu Leu Leu
1               5                   10                  15

Leu Leu Ala Leu Ala Phe Val Leu Phe Tyr Glu Ala Ile Asn Gly Phe
            20                  25                  30

His Asp Thr Ala Asn Ala Val Ala Ala Val Ile Tyr Thr Arg Ala Met
        35                  40                  45

Gln Pro Gln Leu Ala Val Val Met Ala Ala Phe Phe Asn Phe Phe Gly
    50                  55                  60

Val Leu Leu Gly Gly Leu Ser Val Ala Tyr Ala Ile Val His Met Leu
65                  70                  75                  80

Pro Thr Asp Leu Leu Leu Asn Met Gly Ser Thr His Gly Leu Ala Met
                85                  90                  95

Val Phe Ser Met Leu Leu Ala Ala Ile Ile Trp Asn Leu Gly Thr Trp
            100                 105                 110

Phe Phe Gly Leu Pro Ala Ser Ser Ser His Thr Leu Ile Gly Ala Ile
        115                 120                 125

Ile Gly Ile Gly Leu Thr Asn Ala Leu Leu Thr Gly Ser Ser Val Met
    130                 135                 140

Asp Ala Leu Asn Leu Arg Glu Val Thr Lys Ile Phe Ser Ser Leu Ile
145                 150                 155                 160

Val Ser Pro Ile Val Gly Leu Val Ile Ala Gly Gly Leu Ile Phe Leu
                165                 170                 175

Leu Arg Arg Tyr Trp Ser Gly Thr Lys Lys Arg Asp Arg Ile His Arg
            180                 185                 190

Ile Pro Glu Asp Arg Lys Lys Lys Gly Lys Arg Lys Pro Pro Phe
        195                 200                 205

Trp Thr Arg Ile Ala Leu Ile Val Ser Ala Ala Gly Val Ala Phe Ser
    210                 215                 220

His Gly Ala Asn Asp Gly Gln Lys Gly Ile Gly Leu Val Met Leu Val
225                 230                 235                 240

Leu Val Gly Ile Ala Pro Ala Gly Phe Val Val Asn Met Asn Ala Ser
                245                 250                 255

Gly Tyr Glu Ile Thr Arg Thr Arg Asp Ala Val Thr Asn Phe Glu His
            260                 265                 270

Tyr Leu Gln Gln His Pro Glu Leu Pro Gln Lys Leu Ile Ala Met Glu
        275                 280                 285

Pro Pro Leu Pro Ala Ala Ser Thr Asp Gly Thr Gln Val Thr Glu Phe
    290                 295                 300

His Cys His Pro Ala Asn Thr Phe Asp Ala Ile Ala Arg Val Lys Thr
305                 310                 315                 320

Met Leu Pro Gly Asn Met Glu Ser Tyr Glu Pro Leu Ser Val Ser Gln
                325                 330                 335

Arg Ser Gln Leu Arg Arg Ile Met Leu Cys Ile Ser Asp Thr Ser Ala
            340                 345                 350
```

```
Lys Leu Ala Lys Leu Pro Gly Val Ser Lys Glu Asp Gln Asn Leu Leu
            355                 360                 365
Lys Lys Leu Arg Ser Asp Met Leu Ser Thr Ile Glu Tyr Ala Pro Val
370                 375                 380
Trp Ile Ile Met Ala Val Ala Leu Ala Leu Gly Ile Gly Thr Met Ile
385                 390                 395                 400
Gly Trp Arg Arg Val Ala Met Thr Ile Gly Glu Lys Ile Gly Lys Arg
                405                 410                 415
Gly Met Thr Tyr Ala Gln Gly Met Ala Ala Gln Met Thr Ala Ala Val
            420                 425                 430
Ser Ile Gly Leu Ala Ser Tyr Ile Gly Met Pro Val Ser Thr Thr His
        435                 440                 445
Val Leu Ser Ser Ala Val Ala Gly Thr Met Val Val Asp Gly Gly Gly
    450                 455                 460
Leu Gln Arg Lys Thr Val Thr Ser Ile Leu Met Ala Trp Val Phe Thr
465                 470                 475                 480
Leu Pro Ala Ala Ile Phe Leu Ser Gly Gly Leu Tyr Trp Ile Ala Leu
                485                 490                 495
Gln Leu Ile

<210> SEQ ID NO 5
<211> LENGTH: 64
<212> TYPE: DNA
<213> ORGANISM: Artificial Sequence
<220> FEATURE:
<223> OTHER INFORMATION: Primer P1

<400> SEQUENCE: 5
cgccgcgttc atgtcctcaa aatggcgtaa cgtccttgaa gcctgctttt ttatactaag    60
ttgg                                                                  64

<210> SEQ ID NO 6
<211> LENGTH: 64
<212> TYPE: DNA
<213> ORGANISM: Artificial Sequence
<220> FEATURE:
<223> OTHER INFORMATION: Primer P2

<400> SEQUENCE: 6
gtacgattac aggaactgca aggagagcca gtacagcgct caagttagta taaaaagct     60 gaac                                                                  64

<210> SEQ ID NO 7
<211> LENGTH: 1613
<212> TYPE: DNA
<213> ORGANISM: Artificial Sequence
<220> FEATURE:
<223> OTHER INFORMATION: PCR-product 1

<400> SEQUENCE: 7
cgccgcgttc atgtcctcaa aatggcgtaa cgtccttgaa gcctgctttt ttatactaag    60
ttggcattat aaaaaagcat tgcttatcaa tttgttgcaa cgaacaggtc actatcagtc   120
aaaataaaat cattatttga tttcgaattc cccggatccg tcgacctgca ggggggggg    180 ggcgctgagg tctgcctcgt gaagaaggtg ttgctgactc ataccaggcc tgaatcgccc   240
catcatccag ccagaaagtg agggagccac ggttgatgag agctttgttg taggtggacc   300
agttggtgat tttgaacttt tgctttgcca cggaacggtc tgcgttgtcg ggaagatgcg   360
```

```
tgatctgatc cttcaactca gcaaaagttc gatttattca acaaagccgc cgtcccgtca    420
agtcagcgta atgctctgcc agtgttacaa ccaattaacc aattctgatt agaaaaactc    480
atcgagcatc aaatgaaact gcaatttatt catatcagga ttatcaatac catattttg    540 aaaaagccgt ttctgtaatg aaggagaaaa ctcaccgagg cagttccata ggatggcaag    600
atcctggtat cggtctgcga ttccgactcg tccaacatca atacaaccta ttaatttccc    660
ctcgtcaaaa ataaggttat caagtgagaa atcaccatga gtgacgactg aatccggtga    720
gaatggcaaa agcttatgca tttctttcca gacttgttca acaggccagc cattacgctc    780
gtcatcaaaa tcactcgcat caaccaaacc gttattcatt cgtgattgcg cctgagcgag    840
acgaaatacg cgatcgctgt taaaaggaca attacaaaca ggaatcgaat gcaaccggcg    900
caggaacact gccagcgcat caacaatatt ttcacctgaa tcaggatatt cttctaatac    960
ctggaatgct gttttcccgg ggatcgcagt ggtgagtaac catgcatcat caggagtacg    1020
gataaaatgc ttgatggtcg gaagaggcat aaattccgtc agccagttta gtctgaccat    1080
ctcatctgta acatcattgg caacgctacc tttgccatgt ttcagaaaca actctggcgc    1140
atcgggcttc ccatacaatc gatagattgt cgcacctgat gcccgacat tatcgcgagc     1200 ccatttatac ccatataaat cagcatccat gttggaattt aatcgcggcc tcgagcaaga    1260
cgtttcccgt tgaatatggc tcataacacc ccttgtatta ctgtttatgt aagcagacag    1320
ttttattgtt catgatgata tatttttatc ttgtgcaatg taacatcaga gattttgaga    1380
cacaacgtgg ctttcccccc cccccctgca gtctgttaca ggtcactaat accatctaag    1440
tagttgattc atagtgactg catatgttgt gttttacagt attatgtagt ctgttttta     1500 tgcaaaatct aatttaatat attgatattt atatcatttt acgtttctcg ttcagctttt    1560
ttatactaac ttgagcgctg tactggctct ccttgcagtt cctgtaatcg tac           1613
```

<210> SEQ ID NO 8
<211> LENGTH: 20
<212> TYPE: DNA
<213> ORGANISM: Artificial Sequence
<220> FEATURE:
<223> OTHER INFORMATION: Primer P3

<400> SEQUENCE: 8
ataatgcgcc gcgttcatgt                                                 20

<210> SEQ ID NO 9
<211> LENGTH: 21
<212> TYPE: DNA
<213> ORGANISM: Artificial Sequence
<220> FEATURE:
<223> OTHER INFORMATION: Primer P4

<400> SEQUENCE: 9
cgcactatgt cacaatctga a                                               21

<210> SEQ ID NO 10
<211> LENGTH: 1599
<212> TYPE: DNA
<213> ORGANISM: Artificial Sequence
<220> FEATURE:
<223> OTHER INFORMATION: PCR-product 2

<400> SEQUENCE: 10
ataatgcgcc gcgttcatgt cctcaaaatg gcgtaacgtc ctatgctaca tttgtttgct    60
ggcctggatt tgcataccgg gctgttatta ttgcttgcac tggcttttgt gctgttctac    120

| | |
|---|---:|
| gaagccatca atggtttcca tgacacagcc aacgccgtgg caaccgttat ctatacccgc | 180 |
| gcgatgcgtt ctcagctcgc cgtggttatg gcggcggtat tcaactttt gggtgttttg | 240 |
| ctgggtggtc tgagtgttgc ctatgccatt gtgcatatgc tgccgacgga tctgctgctt | 300 |
| aatatgggat cgtctcatgg ccttgccatg gtgttctcta tgttgctggc ggcgattatc | 360 |
| tggaacctgg gtacctggta ctttggttta cctgcatcca gctctcatac gctgattggc | 420 |
| gcgatcatcg ggattggttt aaccaatgcg ttgatgaccg gacgtcagt ggtggatgca | 480 |
| ctcaatatcc cgaaagtatt aagtattttc ggttctctga tcgtttcccc tattgtcggc | 540 |
| ctggtgtttg ctggcggtct gattttcttg ctgcgtcgct actggagcgg caccaagaaa | 600 |
| cgcgcccgta tccacctgac cccagcggag cgtgaaaaga aagacggcaa gaaaaagccg | 660 |
| ccgttctgga cgcgtattgc gctgatcctt tccgctatcg gcgtggcgtt ttcgcacggc | 720 |
| gcgaacgatg gtcagaaagg cattggtctg gttatgttgg tattgattgg cgtcgcgcca | 780 |
| gcaggcttcg tggtgaacat gaatgccact ggctacgaaa tcacccgtac ccgtgatgcc | 840 |
| atcaacaacg tcgaagctta cttttgagcag catcctgcgc tgctcaaaca ggctaccggt | 900 |
| gctgatcagt tagtaccggc tccggaagct ggcgcaacgc aacctgcgga gttccactgc | 960 |
| catccgtcga ataccattaa cgcgctcaac cgcctgaaag gtatgttgac caccgatgtg | 1020 |
| gaaagctacg acaagctgtc gcttgatcaa cgtagccaga tgcgccgcat tatgctgtgc | 1080 |
| gtttctgaca ctatcgacaa agtggtgaag atgcctggcg tgagtgctga cgatcagcgc | 1140 |
| ctgttgaaga aactgaagtc cgacatgctt agcaccatcg agtatgcacc ggtgtggatc | 1200 |
| atcatggcgg tcgcgctggc gttaggtatc ggtacgatga ttggctggcg ccgtgtggca | 1260 |
| acgactatcg gtgagaaaat cggtaagaaa ggcatgacct acgctcaggg gatgtctgcc | 1320 |
| cagatgacgc cggcagtgtc tatcggcctg gcgagttata ccgggatgcc ggtttccact | 1380 |
| actcacgtac tctcctcttc tgtcgcgggg acgatggtgg tagatggtgg cggcttacag | 1440 |
| cgtaaaaccg tgaccagcat tctgatggcc tgggtgttta cccttccggc tgcggtactg | 1500 |
| cttttccggcg ggctgtactg gctctccttg cagttcctgt aatcgtacgc accaaaacga | 1560 |
| gcgggtcagc tggcccgctt cagattgtga catagtgcg | 1599 |

<210> SEQ ID NO 11
<211> LENGTH: 1670
<212> TYPE: DNA
<213> ORGANISM: Artificial Sequence
<220> FEATURE:
<223> OTHER INFORMATION: PCR-product 3

<400> SEQUENCE: 11

| | |
|---|---:|
| ataatgcgcc gcgttcatgt cctcaaaatg gcgtaacgtc cttgaagcct gctttttat | 60 |
| actaagttgg cattataaaa aagcattgct tatcaatttg ttgcaacgaa caggtcacta | 120 |
| tcagtcaaaa taaatcatt atttgatttc gaattcccg gatccgtcga cctgcagggg | 180 |
| gggggggcg ctgaggtctg cctcgtgaag aaggtgttgc tgactcatac caggcctgaa | 240 |
| tcgccccatc atccagccag aaagtgaggg agccacggtt gatgagagct tgttgtagg | 300 |
| tggaccagtt ggtgattttg aacttttgct ttgccacgga acggtctgcg ttgtcgggaa | 360 |
| gatgcgtgat ctgatccttc aactcagcaa aagttcgatt tattcaacaa agccgccgtc | 420 |
| ccgtcaagtc agcgtaatgc tctgccagtg ttacaaccaa ttaaccaatt ctgattagaa | 480 |
| aaactcatcg agcatcaaat gaaactgcaa tttattcata tcaggattat caataccata | 540 |
| tttttgaaaa agccgtttct gtaatgaagg agaaaactca ccgaggcagt tccataggat | 600 |

```
ggcaagatcc tggtatcggt ctgcgattcc gactcgtcca acatcaatac aacctattaa        660
tttcccctcg tcaaaaataa ggttatcaag tgagaaatca ccatgagtga cgactgaatc        720
cggtgagaat ggcaaaagct tatgcatttc tttccagact tgttcaacag gccagccatt        780
acgctcgtca tcaaaatcac tcgcatcaac caaaccgtta ttcattcgtg attgcgcctg        840
agcgagacga aatacgcgat cgctgttaaa aggacaatta caaacaggaa tcgaatgcaa        900
ccggcgcagg aacactgcca gcgcatcaac aatattttca cctgaatcag gatattcttc        960
taatacctgg aatgctgttt tcccggggat cgcagtggtg agtaaccatg catcatcagg       1020
agtacggata aaatgcttga tggtcggaag aggcataaat tccgtcagcc agtttagtct       1080
gaccatctca tctgtaacat cattggcaac gctacctttg ccatgtttca gaaacaactc       1140
tggcgcatcg ggcttcccat acaatcgata gattgtcgca cctgattgcc cgacattatc       1200
gcgagcccat ttatacccat ataaatcagc atccatgttg gaatttaatc gcggcctcga       1260
gcaagacgtt tcccgttgaa tatggctcat aacacccctt gtattactgt ttatgtaagc       1320
agacagtttt attgttcatg atgatatatt tttatcttgt gcaatgtaac atcagagatt       1380
ttgagacaca acgtggcttt cccccccccc cctgcagtct gttacaggtc actaatacca       1440
tctaagtagt tgattcatag tgactgcata tgttgtgttt tacagtatta tgtagtctgt       1500
tttttatgca aaatctaatt taatatattg atatttatat cattttacgt ttctcgttca       1560
gcttttttat actaacttga gcgctgtact ggctctcctt gcagttcctg taatcgtacg       1620
caccaaaacg agcgggtcag ctggcccgct tcagattgtg acatagtgcg                  1670
```

METHOD FOR PRODUCING AN L-AMINO ACID USING A BACTERIUM OF THE FAMILY ENTEROBACTERIACEAE HAVING ATTENUATED EXPRESSION OF A PHOSPHATE TRANSPORTER-ENCODING GENE This application is a Continuation of, and claims priority under 35 U.S.C. §120 to, International Application No. PCT/JP2014/077027, filed Oct. 2, 2014, and claims priority therethrough under 35 U.S.C. §119 to Russian Patent Application No. 2013144250, filed Oct. 2, 2013, the entireties of which are incorporated by reference herein. Also, the Sequence Listing filed electronically herewith is hereby incorporated by reference (File name: 2016-03-28T_US-524_Seq_List; File size: 20 KB; Date recorded: Mar. 28, 2016).

BACKGROUND OF THE INVENTION

1. Field of the Invention

The present invention relates to the microbiological industry, and specifically to a method for producing an L-amino acid by fermentation of a bacterium of the family Enterobacteriaceae that has been modified to attenuate expression of a phosphate transporter-encoding gene.

2. Brief Description of the Related Art

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acid production yields have been reported, including transformation of microorganisms with recombinant DNA (see, for example, U.S. Pat. No. 4,278,765 A), and alteration of regulatory regions such as promoter, leader sequence, and/or attenuator, or others known to the person skilled in the art (see, for example, U.S. Patent Application Publication No. 20060216796 A1 and WO9615246 A1). Other techniques for enhancing production yields include increasing the activities of enzymes involved in amino acid biosynthesis and/or desensitizing the target enzymes to the feedback inhibition by the resulting L-amino acid (see, for example, WO9516042 A1, EP0685555 A1 or U.S. Pat. Nos. 4,346,170 A, 5,661,012 A, and 6,040,160).

Another method for enhancing L-amino acids production yields is to attenuate the expression of a gene or several genes which are involved in the degradation of the target L-amino acid, genes which divert the precursors of the target L-amino acid from the L-amino acid biosynthetic pathway, genes involved in the redistribution of the carbon, nitrogen, and phosphate fluxes, and genes encoding toxins, etc.

Bacteria, such as, for example, *Escherichia coli* (*E. coli*), contain two pit genes, pitA and pitB, which encode proteins that transport inorganic phosphate (Pi) across the cytoplasmic membrane of the bacteria (Harris R. M. et al., Characterization of PitA and PitB from *Escherichia coli*, *J. Bacteriol.*, 2001, 183(17):5008-5014). The phosphate transporters PitA and PitB are protein homologs having an amino acid sequence identity of 81% relative to each other (Hoffer S. M. et al., Activation by gene amplification of pitB, encoding a third phosphate transporter of *Escherichia coli* K-12, *J. Bacteriol.*, 2001, 183(15):4659-4663), and these transporters belong to the Inorganic Phosphate Transporter (PiT) family. A screening of the 34 completely sequenced bacterial genomes (ncbi.nlm.nih.gov/COG) revealed that some bacteria, such as, for example, *Pseudomonas aeruginosa* (Pseudomonadaceae), contain more than one PitA homolog.

The PitA and PitB from the prokaryotic *E. coli* can transport inorganic phosphate independently of each other. Such overlapping activity of inorganic phosphate transporters has been also reported for eukaryotic species such as, for example, *Saccharomyces cerevisiae* (Martinez P. R. et al., Physiological regulation of the derepressible phosphate transporter in *Saccharomyces cerevisiae*, *J. Bacteriol.*, 1998, 180:2253-2256) and *Neurospora crassa* (Versaw W. K. and Metzenberg R. L., Repressible cation-phosphate symporters in *Neurospora crassa*, *Proc. Natl. Acad. Sci. USA*, 1995, 92:3884-3887). Previous studies on prokaryotes have shown that the PitA system, which can also be referred to as the Pit system, mediates the uptake of inorganic phosphate and divalent cation ions. For example, the uptake of inorganic phosphate in *E. coli* (Enterobacteriaceae) and *Acinetobacter johnsonii* (Moraxellaceae) by utilizing the Pit system is dependent on co-transport of divalent metal cation ions, such as Mg(II), Ca(II), Mn(II), or Co(II), through the formation of a soluble, neutral, metal-phosphate complex, which is the transported species (van Veen H. W. et al., Translocation of metal phosphate via the phosphate inorganic transport system of *Escherichia coli*, *Biochemistry*, 1994, 33(7):1766-1770; van Veen H. W. et al., Mechanism and energetics of the secondary phosphate-transport system of *Acinetobacter-johnsonii*-210A. *J. Biol. Chem.*, 1993, 268: 19377-19383). It has been also reported that PitA is involved in Zn(II)-uptake probably via formation of a $ZnHPO_4$ complex. However, it is suggested that PitA may also play the role in Zn(II)-efflux, when the intracellular concentration of zinc ions becomes toxic (Beard S. J. et al., Evidence for the transport of zinc(II) ions via the pit phosphate transport system in *Escherichia coli*, *FEMS Microbiol. Lett.*, 2000, 184:231-235).

However, no data has been previously reported that describes the effect of attenuating expression of a phosphate transporter-encoding gene on production of L-amino acids by fermentation of an L-amino acid-producing bacterium of the family Enterobacteriaceae.

SUMMARY OF THE INVENTION

An aspect of the present invention is to provide an L-amino acid-producing bacterium belonging to the family Enterobacteriaceae, which can belong to the genus *Escherichia* and, more specifically, to the species *E. coli*, which has been modified to attenuate expression of a phosphate transporter-encoding gene, such as the pitA gene or its homolog such as, for example, the pitB gene.

Another aspect of the present invention is to provide a method for producing L-amino acids such as L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine using a bacterium of the family Enterobacteriaceae as described hereinafter.

These aims were achieved by the finding that attenuation of expression of a phosphate transporter-encoding gene, in particular, inactivation of the pitA gene, on the chromosome of an L-amino acid-producing bacterium belonging to the family Enterobacteriaceae, which can belong to the genus *Escherichia* and, more specifically, to the species *Escheri-* chia coli, confers on the bacterium a higher productivity of L-amino acids, such as, for example, L-arginine and L-histidine.

An aspect of the present invention is to provide a method for producing an L-amino acid comprising:

(i) cultivating an L-amino acid-producing bacterium of the family Enterobacteriaceae in a culture medium to produce and accumulate an L-amino acid in the culture medium or cells of the bacterium, or both; and (ii) collecting the L-amino acid from the culture medium or cells of the bacterium, or both, wherein the bacterium has been modified to attenuate expression of a phosphate transporter-encoding gene.

It is a further aspect of the present invention to provide the method as described above, wherein the bacterium belongs to the genus Escherichia.

It is a further aspect of the present invention to provide the method as described above, wherein the bacterium is Escherichia coli.

It is a further aspect of the present invention to provide the method as described above, wherein the bacterium belongs to the genus Pantoea.

It is a further aspect of the present invention to provide the method as described above, wherein the bacterium is Pantoea ananatis.

It is a further aspect of the present invention to provide the method as described above, wherein the expression of the phosphate transporter-encoding gene is attenuated by inactivation of the phosphate transporter-encoding gene.

It is a further aspect of the present invention to provide the method as described above, wherein the phosphate transporter-encoding gene is deleted.

It is a further aspect of the present invention to provide the method as described above, wherein the phosphate transporter-encoding gene is selected from the group consisting of:

(A) a DNA comprising the nucleotide sequence of SEQ ID NO: 1;

(B) a DNA comprising the nucleotide sequence of SEQ ID NO: 3;

(C) a DNA comprising a variant nucleotide sequence of SEQ ID NO: 1 or SEQ ID NO: 3 due to the degeneracy of the genetic code;

(D) a DNA having an identity of the nucleotide sequence of not less than 75% with respect to the entire nucleotide sequence of SEQ ID NO: 1 or SEQ ID NO: 3, and wherein said nucleotide sequence encodes a protein having inorganic phosphate-transporting activity;

(E) a DNA encoding a protein comprising the amino acid sequence of SEQ ID NO: 2;

(F) a DNA encoding a protein comprising the amino acid sequence of SEQ ID NO: 4; and (G) a DNA encoding a protein comprising the amino acid sequence of SEQ ID NO: 2 or SEQ ID NO: 4, but wherein said sequence includes substitutions, deletions, insertions, or additions of one or several amino acid residues, and wherein said protein has inorganic phosphate-transporting activity.

It is a further aspect of the present invention to provide the method as described above, wherein the L-amino acid is selected from the group consisting of an aromatic L-amino acid and a non-aromatic L-amino acid.

It is a further aspect of the present invention to provide the method as described above, wherein the aromatic L-amino acid is selected from the group consisting of L-phenylalanine, L-tryptophan, and L-tyrosine.

It is a further aspect of the present invention to provide the method as described above, wherein the non-aromatic L-amino acid is selected from the group consisting of L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-proline, L-serine, L-threonine, and L-valine.

It is a further aspect of the present invention to provide the method as described above, wherein the L-amino acid is L-arginine and L-histidine.

BRIEF DESCRIPTION OF THE DRAWINGS

FIG. 1 shows the scheme of the pMW118-λattL-Km$^R$-λattR plasmid.

DESCRIPTION OF THE PREFERRED EMBODIMENTS

The present invention is described in detail below.

1. Bacterium

The phrase "an L-amino acid-producing bacterium" can mean a bacterium of the family Enterobacteriaceae that has an ability to produce, excrete or secrete, and/or cause accumulation of an L-amino acid in a culture medium or the bacterial cells when the bacterium is cultured in the medium.

The phrase "an L-amino acid-producing bacterium" can also mean a bacterium that is able to produce, excrete or secrete, and/or cause accumulation of an L-amino acid in a culture medium in an amount larger than a wild-type or parental strain, such as E. coli K-12. The phrase "an L-amino acid-producing bacterium" can also mean a bacterium that is able to cause accumulation in a culture medium of an amount not less than 0.5 g/L or not less than 1.0 g/L of the target L-amino acid. The bacterium can produce either one kind of amino acid solely, or a mixture of two or more kinds of amino acids.

The phrase "L-amino acid-producing ability" can mean the ability of the bacterium to produce, excrete or secrete, and/or cause accumulation of the L-amino acid in a culture medium or the bacterial cells to such a level that the L-amino acid can be collected from the culture medium or the bacterial cells, when the bacterium is cultured in the medium.

The phrase "L-amino acid" can mean L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine.

The phrase "aromatic L-amino acid" includes, for example, L-phenylalanine, L-tryptophan, and L-tyrosine. As L-histidine has an aromatic moiety, specifically, an imidazole ring, the phrase "aromatic L-amino acid" can also include, besides the aforementioned aromatic L-amino acids, L-histidine.

The phrase "non-aromatic L-amino acid" includes, for example, L-alanine, L-arginine, L-asparagine, L-aspartic acid, L-citrulline, L-cysteine, L-glutamic acid, L-glutamine, glycine, L-isoleucine, L-leucine, L-lysine, L-methionine, L-ornithine, L-proline, L-serine, L-threonine, and L-valine. As the biosynthetic pathway of L-histidine is different from the biosynthetic pathways of common aromatic amino acids such as L-phenylalanine, L-tryptophan, and L-tyrosine, the phrase "non-aromatic L-amino acid" can also include, besides the aforementioned non-aromatic L-amino acids, L-histidine.

That is, L-histidine can be included in either one of, or both of "aromatic L-amino acid" and "non-aromatic L-amino acid".

An L-amino acid can belong to one or more L-amino acid families. As an example, the glutamate family includes L-arginine, L-glutamic acid, L-glutamine, and L-proline; the serine family includes L-cysteine, glycine, and L-serine; the aspartate family includes L-asparagine, L-aspartic acid, L-isoleucine, L-lysine, L-methionine, and L-threonine; the pyruvate family includes L-alanine, L-isoleucine, L-valine, and L-leucine; and the aromatic family includes L-phenylalanine, L-tryptophan, and L-tyrosine. As an L-amino acid can be an intermediate in a biosynthetic pathway of another L-amino acid, the aforementioned families of amino acids may also include other L-amino acids, such as, for example, non-proteinogenic L-amino acids. For example, L-citrulline and L-ornithine are amino acids from the L-arginine biosynthetic pathway. Therefore, the glutamate family may include L-arginine, L-citrulline, L-glutamic acid, L-glutamine, L-ornithine, and L-proline.

L-Arginine, L-cysteine, L-glutamic acid, L-glutamine, L-histidine, L-isoleucine, L-lysine, L-ornithine, L-phenylalanine, L-proline, L-threonine, L-tryptophan, and L-valine are particular examples. L-Arginine, L-glutamine, L-histidine, and L-proline are specific examples. L-arginine and L-histidine are more specific examples.

The phrase "L-amino acid" can include not only an L-amino acid in a free form, but may also include a salt or a hydrate thereof, or an adduct form thereof with another organic or inorganic compound as described hereinafter.

The bacteria belonging to the family Enterobacteriaceae can be from the genera *Escherichia* and/or *Pantoea*, and so forth, and can have the ability to produce an L-amino acid. Specifically, those classified into the family Enterobacteriaceae according to the taxonomy used in the NCBI (National Center for Biotechnology Information) database (www.ncbi.nlm.nih.gov/Taxonomy/Browser/wwwtax-.cgi?id=543) can be used. Examples of strains from the family Enterobacteriaceae that can be modified include a bacterium of the genus *Escherichia, Enterobacter,* or *Pantoea*.

Strains of *Escherichia* bacterium which can be modified to obtain *Escherichia* bacteria in accordance with the presently disclosed subject matter are not particularly limited, and specifically, those described in the work of Neidhardt et al. can be used (Bachmann, B. J., Derivations and genotypes of some mutant derivatives of *E. coli* K-12, p. 2460-2488. In F. C. Neidhardt et al. (ed.), *E. coli* and *Salmonella*: cellular and molecular biology, 2$^{nd}$ ed. ASM Press, Washington, D.C., 1996). The species *E. coli* is a particular example. Specific examples of *E. coli* include *E. coli* W3110 (ATCC 27325), *E. coli* MG1655 (ATCC 47076), and so forth, which are derived from the prototype wild-type strain, *E. coli* K-12 strain. These strains are available from, for example, the American Type Culture Collection (P.O. Box 1549, Manassas, Va. 20108, United States of America). That is, registration numbers are given to each of the strains, and the strains can be ordered by using these registration numbers (refer to atcc.org). The registration numbers of the strains are listed in the catalogue of the American Type Culture Collection.

Examples of the *Enterobacter* bacteria include *Enterobacter agglomerans, Enterobacter aerogenes*, and so forth. Examples of the *Pantoea* bacteria include *Pantoea ananatis*, and so forth. Some strains of *Enterobacter agglomerans* were recently reclassified into *Pantoea agglomerans, Pantoea ananatis*, or *Pantoea stewartii* on the basis of nucleotide sequence analysis of 16S rRNA, etc. A bacterium belonging to any of the genus *Enterobacter* or *Pantoea* may be used so long as it is a bacterium classified into the family Enterobacteriaceae. When a *Pantoea ananatis* strain is bred by genetic engineering techniques, *Pantoea ananatis* AJ13355 strain (FERM BP-6614), AJ13356 strain (FERM BP-6615), AJ13601 strain (FERM BP-7207), and derivatives thereof can be used. These strains were identified as *Enterobacter agglomerans* when they were isolated, and deposited as *Enterobacter agglomerans*. However, they were recently re-classified as *Pantoea ananatis* on the basis of nucleotide sequencing of 16S rRNA and so forth as described above.

L-Amino Acid-Producing Bacteria

The bacterium of the present invention belonging to the family Enterobacteriaceae and modified to attenuate expression of a phosphate transporter-encoding gene, such as pitA or its homolog pitB, which is able to produce an L-amino acid, can be used.

The bacterium may inherently have the L-amino acid-producing ability or may be modified to have an L-amino acid-producing ability by using a mutation method or DNA recombination techniques. The bacterium can be obtained by attenuating expression of a phosphate transporter-encoding gene in a bacterium inherently having the ability to produce an L-amino acid. Alternatively, the bacterium can be obtained by imparting the ability to produce an L-amino acid to a bacterium already having a phosphate transporter-encoding gene attenuated. Also, the bacterium can be a bacterium that has acquired the ability to produce an L-amino acid by attenuating expression of a phosphate transporter-encoding gene.

The bacterium can produce an L-amino acid either alone or as a mixture of two or more kinds of L-amino acids. It is also acceptable that the bacterium can produce an L-amino acid either alone or as a mixture of the L-amino acid and a salt thereof, as explained hereinafter.

Hereafter, L-amino acid-producing bacteria will be specifically exemplified. Any of the properties of the L-amino acid-producing bacteria and modifications for imparting or enhancing an L-amino acid-producing ability, such as those exemplified below, can be used independently or in any appropriate combination.

L-Arginine-Producing Bacteria

Examples of L-arginine-producing bacteria and parental strains which can be used to derive L-arginine-producing bacteria include, but are not limited to, strains belonging to the genus *Escherichia* such as *E. coli* strain 237 (VKPM B-7925) (U.S. Patent Application No. 2002058315 A1) and its derivative strains harboring mutant argA genes encoding mutant N-acetylglutamate synthase (Russian Patent No. 2215783 C2, EP1170361 A1), *E. coli* strain 382 (VKPM B-7926, EP1170358 A1), *E. coli* strain 382 ilvA+, which is obtained from the strain 382 by introducing the wild-type allele of ilvA gene from *E. coli* K-12 strain thereto, and the like. Examples of mutant N-acetylglutamate synthase include, for example, a mutant N-acetylglutamate synthase desensitized to feedback inhibition by L-arginine by substitution for the amino acid residues corresponding to the positions 15 to 19 of the wild type enzyme (EP1170361 A1).

Examples of L-arginine-producing bacteria and parental strains which can be used to derive L-arginine-producing bacteria also include strains in which expression of one or more genes encoding an L-arginine biosynthetic enzyme are enhanced. Examples of such genes include genes encoding N-acetyl-γ-glutamylphosphate reductase (argC), ornithine acetyltransferase (argJ), N-acetylglutamate kinase (argB), N-acetylornithine aminotransferase (argD), ornithine carbamoyltransferase (argF), argininosuccinate synthase (argG), argininosuccinate lyase (argH), and carbamoyl phosphate synthetase (carAB), in addition to the gene encoding N-acetylglutamate synthase (argA). The argA gene may also be a mutant argA gene encoding mutant N-acetylglutamate synthase such as those exemplified above.

Examples of L-arginine-producing bacteria and parental strains which can be used to derive L-arginine-producing bacteria also include strains having resistance to amino acid analogues, and so forth. Examples of such strains include *Escherichia coli* mutant strains having resistance to α-methylmethionine, p-fluorophenylalanine, D-arginine, arginine hydroxamate, S-(2-aminoethyl)-cysteine, α-methylserine, β-2-thienylalanine, or sulfaguanidine (refer to Japanese Patent Laid-open (Kokai) No. 56-106598).

L-Citrulline-Producing Bacteria

Examples of L-citrulline-producing bacteria and parental strains which can be used to derive L-citrulline-producing bacteria include, but are not limited to, strains belonging to the genus *Escherichia* such as *E. coli* mutant N-acetylglutamate synthase strains 237/pMADS11, 237/pMADS12, and 237/pMADS13 (RU2215783 C2, European Patent No. 1170361 B1, U.S. Pat. No. 6,790,647 B2), *E. coli* strains 333 (VKPM B-8084) and 374 (VKPM B-8086), both harboring mutant feedback-resistant carbamoyl phosphate synthetase (Russian Patent No. 2264459 C2), *E. coli* strains in which α-ketoglutarate synthase activity is increased, and ferredoxin NADP$^+$ reductase, pyruvate synthase, and/or α-ketoglutarate dehydrogenase activities are additionally modified (EP2133417 A1), and strain *P. ananantis* NAlsucAsdhA, in which succinate dehydrogenase and α-ketoglutarate dehydrogenase activities are decreased (U.S. Patent Application No. 2009286290 A1), and the like.

As L-citrulline is an intermediate of L-arginine biosynthetic pathway, examples of L-citrulline-producing bacteria and parent strains which can be used to derive L-citrulline-producing bacteria, include strains in which expression of one or more genes encoding an L-arginine biosynthetic enzyme is enhanced. Examples of such genes include, but are not limited to, genes encoding N-acetylglutamate synthase (argA), N-acetylglutamate kinase (argB), N-acetylglutamyl phosphate reductase (argC), acetylornithine transaminase (argD), acetylornithine deacetylase (argE), ornithine carbamoyltransferase (argF/I), and carbamoyl phosphate synthetase (carAB), and combinations thereof An L-citrulline-producing bacterium can be also easily obtained from any L-arginine-producing bacterium, for example *E. coli* 382 stain (VKPM B-7926), by inactivation of argininosuccinate synthase encoded by argG gene.

L-Cysteine-Producing Bacteria

Examples of L-cysteine-producing bacteria and parental strains which can be used to derive L-cysteine-producing bacteria include, but are not limited to, strains belonging to the genus *Escherichia* such as *E. coli* JM15 transformed with different cysE alleles encoding feedback-resistant serine acetyltransferases (U.S. Pat. No. 6,218,168 B1, Russian Patent No. 2279477 C2), *E. coli* W3110 having overexpressed genes which encode proteins suitable for secreting substances toxic for cells (U.S. Pat. No. 5,972,663 A), *E. coli* strains having a lowered cysteine desulfohydrase activity (JP11155571 A2), *E. coli* W3110 having an increased activity of a positive transcriptional regulator for cysteine regulon encoded by the cysB gene (WO0127307 A1), and the like.

L-Glutamic Acid-Producing Bacteria

Examples of L-glutamic acid-producing bacteria and parental strains which can be used to derive L-glutamic acid-producing bacteria include, but are not limited to, strains belonging to the genus *Escherichia* such as *E. coli* VL334thrC$^+$ (EP 1172433 A1). The *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* strain K-12 (VKPM B-7) cells. As a result, an L-isoleucine auxotrophic strain VL334thrC$^+$ (VKPM B-8961), which is able to produce L-glutamic acid, was obtained.

Examples of L-glutamic acid-producing bacteria and parental strains which can be used to derive the L-glutamic acid-producing bacteria include, but are not limited to strains in which expression of one or more genes encoding an L-glutamic acid biosynthetic enzyme are enhanced. Examples of such genes include genes encoding glutamate dehydrogenase (gdhA), glutamine synthetase (glnA), glutamate synthetase (gltBD), isocitrate dehydrogenase (icdA), aconitate hydratase (acnA, acnB), citrate synthase (OA), phosphoenolpyruvate carboxylase (ppc), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgml), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), and glucose phosphate isomerase (pgi).

Examples of strains modified so that expression of the citrate synthetase gene, the phosphoenolpyruvate carboxylase gene, and/or the glutamate dehydrogenase gene is/are enhanced include those disclosed in EP1078989 A2, EP955368 A2, and EP952221 A2.

Examples of L-glutamic acid-producing bacteria and parental strains which can be used to derive the L-glutamic acid-producing bacteria also include strains having a decreased or eliminated activity of an enzyme that catalyzes synthesis of a compound other than L-glutamic acid by branching off from an L-glutamic acid biosynthesis pathway. Examples of such enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), glutamate decarboxylase (gadA), succinate dehydrogenase (sdhABCD), and 1-pyroline-5-carboxylate dehydrogenase (putA). Bacteria belonging to the genus *Escherichia* deficient in the α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

*E. coli* W3110sucA::Km$^R$
  *E. coli* AJ12624 (FERM BP-3853)
  *E. coli* AJ12628 (FERM BP-3854)
  *E. coli* AJ12949 (FERM BP-4881)

*E. coli* W3110sucA::Km$^R$ is a strain obtained by disrupting the α-ketoglutarate dehydrogenase gene (hereinafter referred to as "sucA gene") of *E. coli* W3110. This strain is completely deficient in the α-ketoglutarate dehydrogenase.

Other examples of L-glutamic acid-producing bacteria and parental strains which can be used to derive the L-glutamic acid-producing bacteria include strains that belong to the genus *Escherichia* and have resistance to an aspartic acid antimetabolite. These strains can also be deficient in the α-ketoglutarate dehydrogenase activity and examples thereof include, for example, *E. coli* AJ13199 (FERM BP-5807) (U.S. Pat. No. 5,908,768), *E. coli* FFRM P-12379, which additionally has a lowered L-glutamic acid-decomposing ability (U.S. Pat. No. 5,393,671), *E. coli* AJ13138 (FERM BP-5565) (U.S. Pat. No. 6,110,714), and the like.

Examples of L-glutamic acid-producing bacteria and parental strains which can be used to derive the L-glutamic acid-producing bacteria also include *Pantoea* bacteria, such as the *Pantoea ananatis* AJ13355 strain (FERM BP-6614), *Pantoea ananatis* SC17 strain (FERM BP-11091), and *Pantoea ananatis* SC17(0) strain (VKPM B-9246). The AJ13355 strain is isolated from soil in Iwata-shi, Shizuoka-ken, Japan as a strain that can proliferate in a low pH medium containing L-glutamic acid and a carbon source. The SC17 strain is selected as a low phlegm-producing mutant strain from the AJ13355 strain (U.S. Pat. No. 6,596,517). The SC17 strain was deposited at the independent administrative agency, National Institute of Advanced Industrial Science and Technology, International Patent Organism Depository (currently independent administrative agency, National Institute of Technology and Evaluation, International Patent Organism Depositary, #120, 2-5-8 Kazusakamatari, Kisarazu-shi, Chiba-ken, 292-0818, Japan) on Feb. 4, 2009, and assigned an accession number of FERM BP-11091. The AJ13355 strain was deposited at the National Institute of Bioscience and Human Technology, Agency of Industrial Science and Technology (currently, independent administrative agency, National Institute of Technology and Evaluation, International Patent Organism Depositary (NITE IPOD), #120, 2-5-8 Kazusakamatari, Kisarazu-shi, Chiba-ken, 292-0818, Japan) on Feb. 19, 1998 and assigned an accession number of FERM P-16644. Then, the deposit was converted to an international deposit under the provisions of Budapest Treaty on Jan. 11, 1999, and assigned an accession number of FERM BP-6614.

Examples of L-glutamic acid-producing bacteria and parental strains which can be used to derive the L-glutamic acid-producing bacteria also include mutant strains belonging to the genus *Pantoea* that are deficient in the α-ketoglutarate dehydrogenase activity or have a decreased α-ketoglutarate dehydrogenase activity, and can be obtained as described above. Such strains include *Pantoea ananatis* AJ13356. (U.S. Pat. No. 6,331,419 B1). *Pantoea ananatis* AJ13356 was deposited at the National Institute of Bioscience and Human-Technology, Agency of Industrial Science and Technology, Ministry of International Trade and Industry (currently NITE IPOD, #120, 2-5-8 Kazusakamatari, Kisarazu-shi, Chiba-ken, 292-0818, Japan) on Feb. 19, 1998 under the accession number FERM P-16645. It was then converted to an international deposit under the provisions of Budapest Treaty on Jan. 11, 1999 and received an accession number of FERM BP-6615. *Pantoea ananatis* AJ13356 is deficient in α-ketoglutarate dehydrogenase activity as a result of disruption of the αKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

Examples of L-glutamic acid-producing bacteria and parental strains which can be used to derive the L-glutamic acid-producing bacteria also include strains belonging to the genus *Pantoea* such as the *Pantoea ananatis* SC17sucA/RSFCPG+pSTVCB strain, *Pantoea ananatis* AJ13601 strain, *Pantoea ananatis* NP106 strain, and *Pantoea ananatis* NA1 strain. The SC17sucA/RSFCPG+pSTVCB strain was obtained by introducing the plasmid RSFCPG containing the citrate synthase gene (OA), phosphoenolpyruvate carboxylase gene (ppc), and glutamate dehydrogenase gene (gdhA) derived from *Escherichia coli*, and the plasmid pSTVCB containing the citrate synthase gene (OA) derived from *Brevibacterium lactofermentum*, into the SC17sucA strain. The AJ13601 strain is selected from the SC17sucA/RSFCPG+pSTVCB strain as a strain resistant to a high concentration of L-glutamic acid at a low pH. The NP 106 strain was obtained from the AJ13601 strain by curing the RSFCPG and pSTVCB plasmids. The AJ13601 strain was deposited at the National Institute of Bioscience and Human Technology, Agency of Industrial Science and Technology (currently, NITE IPOD, #120, 2-5-8 Kazusakamatari, Kisarazu-shi, Chiba-ken, 292-0818, Japan) on Aug. 18, 1999, and assigned an accession number FERM P-17516. Then, the deposit was converted to an international deposit under the provisions of the Budapest Treaty on Jul. 6, 2000, and assigned an accession number FERM BP-7207.

Examples of L-glutamic acid-producing bacteria and parental strains which can be used to derive the L-glutamic acid-producing bacteria also include strains having resistance to an aspartic acid analogue. Such strains can also be deficient in the α-ketoglutarate dehydrogenase activity. Specific examples of strains having resistance to an aspartic acid analogue and deficient in the α-ketoglutarate dehydrogenase activity include, for example, *E. coli* AJ13199 (FERM BP-5807, U.S. Pat. No. 5,908,768), *E. coli* FFRM P-12379, which additionally has a lowered L-glutamic acid-decomposing ability (U.S. Pat. No. 5,393,671), and *E. coli* AJ13138 (FERM BP-5565, U.S. Pat. No. 6,110,714).

L-Histidine-Producing Bacteria

Examples of L-histidine-producing bacteria and parental strains which can be used to derive L-histidine-producing bacteria include, but are not limited to, strains belonging to the genus *Escherichia* such as *E. coli* strain 24 (VKPM B-5945, RU2003677 C1), *E. coli* strain 80 (VKPM B-7270, RU2119536 C1), *E. coli* NRRL B-12116-B-12121 (U.S. Pat. No. 4,388,405), *E. coli* H-9342 (FERM BP-6675) and H-9343 (FERM BP-6676) (U.S. Pat. No. 6,344,347 B1), *E. coli* H-9341 (FERM BP-6674) (EP1085087 A2), *E. coli* AI80/pFM201 (U.S. Pat. No. 6,258,554 B1), and the like.

Examples of L-histidine-producing bacteria and parental strains which can be used to derive L-histidine-producing bacteria also include strains in which expression of one or more genes encoding an L-histidine biosynthetic enzyme are enhanced. Examples of such genes include genes encoding ATP phosphoribosyltransferase (hisG), phosphoribosyl-AMP cyclohydrolase (hisI), phosphoribosyl-AMP cyclohydrolase/phosphoribosyl-ATP pyrophosphatase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore an L-histidine-producing ability can also be efficiently enhanced by introducing a mutation conferring resistance to the feedback inhibition into ATP phosphoribosyltransferase (Russian Patent Nos. 2003677 C1 and 2119536 C1).

Specific examples of strains having an L-histidine-producing ability include *E. coli* FERM-P 5038 and 5048, which have been transformed with a vector carrying a DNA encoding an L-histidine-biosynthetic enzyme (JP 56-005099

A), *E. coli* strains transformed with rht, a gene for an amino acid-export (EP1016710 A2), *E. coli* 80 strain, which has been imparted with sulfaguanidine, DL-1,2,4-triazole-3-alanine, and streptomycin-resistance (VKPM B-7270, RU2119536 C1), *E. coli* MG1655+hisGr hisL'_Δ ΔpurR (RU2119536 and Doroshenko V. G. et al., The directed modification of *Escherichia coli* MG1655 to obtain histidine-producing mutants, *Prikl. Biochim. Mikrobiol.* (Russian), 2013, 49(2):149-154.), and so forth.

L-Isoleucine-Producing Bacteria

Examples of L-isoleucine-producing bacteria and parental strains which can be used to derive L-isoleucine-producing bacteria include, but are not limited to, mutant strains having resistance to 6-dimethylaminopurine (JP 5-304969 A), mutant strains having resistance to an isoleucine analogue such as thiaisoleucine and isoleucine hydroxamate, and mutant strains additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as L-isoleucine-producing bacteria or parental strains (JP 2-458 A, EP0356739 A1, and U.S. Pat. No. 5,998,178).

L-Leucine-Producing Bacteria

Examples of L-leucine-producing bacteria and parental strains which can be used to derive L-leucine-producing bacteria include, but are not limited to, strains belonging to the genus *Escherichia* such as *E. coli* strains resistant to leucine (for example, the strain 57 (VKPM B-7386, U.S. Pat. No. 6,124,121)); *E. coli* strains resistant to leucine analogs including β-2-thienylalanine, 3-hydroxyleucine, 4-azaleucine, 5,5,5-trifluoroleucine (JP 62-34397 B and JP 8-70879 A); *E. coli* strains obtained by the gene engineering method described in WO96/06926; *E. coli* H-9068 (JP 8-70879 A), and the like.

Examples of L-leucine-producing bacteria and parental strains which can be used to derive L-leucine-producing bacteria also include strains in which the expression of one or more genes involved in L-leucine biosynthesis is enhanced. Examples of such genes include genes of the leuABCD operon, which can be represented by a mutant leuA gene encoding α-isopropylmalate synthase freed from feedback inhibition by L-leucine (U.S. Pat. No. 6,403,342 B1). In addition, examples of L-leucine-producing bacteria and parental strains which can be used to derive L-leucine-producing bacteria also include strains in which the expression of one or more genes encoding proteins which excrete L-amino acid from the bacterial cell is enhanced. Examples of such genes include the b2682 and b2683 genes (ygaZH genes) (EP1239041 A2).

L-Lysine-Producing Bacteria

Examples of L-lysine-producing bacteria and parental strains which can be used to derive L-lysine-producing bacteria include mutant strains belonging to the genus *Escherichia* and having resistance to an L-lysine analogue. The L-lysine analogue inhibits growth of bacteria belonging to the genus *Escherichia*, but this inhibition is fully or partially desensitized when L-lysine is present in the medium. Examples of the L-lysine analogue include, but are not limited to, oxalysine, lysine hydroxamate, S-(2-aminoethyl)-L-cysteine (AEC), γ-methyllysine, α-chlorocaprolactam, and so forth. Mutant strains having resistance to these lysine analogues can be obtained by subjecting bacteria belonging to the genus *Escherichia* to a conventional artificial mutagenesis treatment. Specific examples of bacterial strains useful for producing L-lysine include *E. coli* AJ11442 (FERM BP-1543, NRRL B-12185; see U.S. Pat. No. 4,346,170) and *E. coli* VL611. In these strains, feedback inhibition of aspartokinase by L-lysine is desensitized.

Examples of L-lysine-producing bacteria and parental strains which can be used to derive L-lysine-producing bacteria also include strains in which expression of one or more genes encoding an L-lysine biosynthetic enzyme is enhanced. Examples of such genes include, but are not limited to, genes encoding dihydrodipicolinate synthase (dapA), aspartokinase III (lysC), dihydrodipicolinate reductase (dapB), diaminopimelate decarboxylase (lysA), diaminopimelate dehydrogenase (ddh)(U.S. Pat. No. 6,040,160), phosphoenolpyruvate carboxylase (ppc), aspartate semialdehyde dehydrogenase (asd), and aspartase (aspA) (EP1253195 A1). In addition, the parental strains may have an increased level of expression of the gene involved in energy efficiency (cyo) (EP1170376 A1), the gene encoding nicotinamide nucleotide transhydrogenase (pntAB) (U.S. Pat. No. 5,830,716 A), the ybjE gene (WO2005/073390), or combinations thereof. Since aspartokinase III is subjected to feedback inhibition by L-lysine, a mutant lysC gene coding for an aspartokinase III desensitized to feedback inhibition by L-lysine (U.S. Pat. No. 5,932,453) may be used for enhancing the activity of this enzyme. Further, since dihydrodipicolinate synthase is subjected to feedback inhibition by L-lysine, a mutant dapA gene coding for a dihydrodipicolinate synthase desensitized to feedback inhibition by L-lysine may be used for enhancing the activity of this enzyme.

L-lysine-producing bacteria or parental strains which can be used to derive L-lysine-producing bacteria may have a reduced or no activity of an enzyme that catalyzes a reaction which causes a branching off from the L-amino acid biosynthesis pathway and results in the production of another compound. Also, L-lysine-producing bacteria or parental strains which can be used to derive L-lysine-producing bacteria may have a reduced or no activity of an enzyme that negatively acts on L-lysine synthesis or accumulation. Examples of such enzymes involved in L-lysine production include homoserine dehydrogenase, lysine decarboxylase (cadA, ldcC), malic enzyme, and so forth, and strains in which activities of these enzymes are decreased or deleted are disclosed in WO95/23864, WO96/17930, WO2005/010175, and so forth.

Expression of both the cadA and ldcC genes encoding lysine decarboxylase can be decreased in order to decrease or delete the lysine decarboxylase activity. Expression of the both genes can be decreased by, for example, the method described in WO2006/078039.

Examples of L-lysine-producing bacteria and parental strains which can be used to derive L-lysine-producing bacteria also include the *E. coli* WC196 strain (U.S. Pat. No. 5,827,698), the *E. coli* WC196ΔcadAΔldc strain, and the *E. coli* WC196ΔcadAΔldcC/pCABD2 strain (WO2006/078039).

The WC196 strain was bred from the W3110 strain, which was derived from *E. coli* K-12, by conferring AEC resistance to the W3110 strain (U.S. Pat. No. 5,827,698). The WC196 strain was designated *E. coli* AJ13069, deposited at the National Institute of Bioscience and Human-Technology, Agency of Industrial Science and Technology (currently NITE IPOD, #120, 2-5-8 Kazusakamatari, Kisarazu-shi, Chiba-ken, 292-0818, Japan) on Dec. 6, 1994, and assigned an accession number of FERM P-14690. Then, it was converted to an international deposit under the provisions of the Budapest Treaty on Sep. 29, 1995, and assigned an accession number of FERM BP-5252 (U.S. Pat. No. 5,827, 698).

The WC196ΔcadAΔldc strain was constructed from the WC196 strain by disrupting the cadA and ldcC genes which encode lysine decarboxylase. The WC196ΔcadAΔldcC was designated AJ110692 and deposited at the National Institute of Bioscience and Human-Technology, Agency of Industrial Science and Technology (currently NITE IPOD, #120, 2-5-8 Kazusakamatari, Kisarazu-shi, Chiba-ken, 292-0818, Japan) on Oct. 7, 2008 as an international deposit under the accession number FERM BP-11027.

The WC196ΔcadAΔldcC/pCABD2 strain was constructed by introducing the plasmid pCABD2 containing lysine biosynthesis genes (U.S. Pat. No. 6,040,160) into the WC196ΔcadAΔldcC strain. The plasmid pCABD2 contains a mutant dapA gene derived from *Escherichia coli* and coding for a dihydrodipicolinate synthase (DDPS) having a mutation for desensitization to feedback inhibition by L-lysine, a mutant lysC gene derived from *Escherichia coli* and coding for aspartokinase III having a mutation for desensitization to feedback inhibition by L-lysine, the dapB gene derived from *Escherichia coli* and coding for dihydrodipicolinate reductase, and the ddh gene derived from *Brevibacterium lactofermentum* and coding for diaminopimelate dehydrogenase.

Examples of L-lysine-producing bacteria and parental strains which can be used to derive L-lysine-producing bacteria also include *E. coli* AJIK01 (NITE BP-01520). The AJIK01 strain was designated *E. coli* AJ111046, and deposited at NITE IPOD (#120, 2-5-8 Kazusakamatari, Kisarazu-shi, Chiba-ken, 292-0818, Japan) on Jan. 29, 2013. Then, it was converted to an international deposit under the provisions of the Budapest Treaty on May 15, 2014, and assigned an accession number of NITE BP-01520.

L-Methionine-Producing Bacteria

Examples of L-methionine-producing bacteria and parent strains which can be used to derive L-methionine-producing bacteria include, but are not limited to, strains belonging to the genus *Escherichia* such as *E. coli* strains AJ11539 (NRRL B-12399), AJ11540 (NRRL B-12400), AJ11541 (NRRL B-12401), AJ 11542 (NRRL B-12402) (Patent GB2075055); and *E. coli* strains 218 (VKPM B-8125) (RU2209248 C2) and 73 (VKPM B-8126) (RU2215782 C2) resistant to norleucine, the L-methionine analog, or the like. The strain *E. coli* 73 was deposited in the Russian National Collection of Industrial Microorganisms (VKPM) (Russian Federation, 117545 Moscow, 1$^{st}$ Dorozhny Proezd, 1) on May 14, 2001 under the accession number VKPM B-8126, and was converted to an international deposit under the Budapest Treaty on Feb. 1, 2002. Furthermore, a methionine repressor-deficient strain and recombinant strains transformed with genes encoding proteins involved in L-methionine biosynthesis such as homoserine transsuccinylase and cystathionine γ-synthase (JP 2000-139471 A) can also be used as L-methionine-producing bacteria or parent strains.

L-Ornithine-Producing Bacteria

As L-ornithine is an intermediate of L-arginine biosynthetic pathway, examples of L-ornithine-producing bacteria and parent strains which can be used to derive L-ornithine-producing bacteria, include strains in which expression of one or more genes encoding an L-arginine biosynthetic enzyme, such as those described above, is enhanced.

An L-ornithine-producing bacterium can be easily obtained from any L-arginine-producing bacterium, for example *E. coli* 382 strain (VKPM B-7926), by inactivation of ornithine carbamoyltransferase encoded by both argF and argI genes. Methods for inactivation of ornithine carbamoyltransferase are described herein.

L-Phenylalanine-Producing Bacteria

Examples of L-phenylalanine-producing bacteria and parental strains which can be used to derive L-phenylalanine-producing bacteria include, but are not limited to, strains belonging to the genus *Escherichia* such as *E. coli* AJ12739 (tyrA::Tn10, tyrR) (VKPM B-8197), *E. coli* HW1089 (ATCC 55371) harboring the mutant pheA34 gene (U.S. Pat. No. 5,354,672), *E. coli* MWEC101-b (KR8903681), *E. coli* NRRL B-12141, NRRL B-12145, NRRL B-12146, and NRRL B-12147 (U.S. Pat. No. 4,407, 952), *E. coli* K-12 [W3110 (tyrA)/pPHAB] (FERM BP-3566), *E. coli* K-12 [W3110 (tyrA)/pPHAD] (FERM BP-12659), *E. coli* K-12 [W3110 (tyrA)/pPHATerm] (FERM BP-12662), and *E. coli* K-12 [W3110 (tyrA)/pBR-aroG4, pACMAB] named as AJ12604 (FERM BP-3579) (EP488424 B1). Furthermore, L-phenylalanine-producing bacteria and parental strains which can be used to derive L-phenylalanine-producing bacteria also include strains belonging to the genus *Escherichia* and having an enhanced activity of the protein encoded by the yedA gene or the yddG gene (U.S. Patent applications 20030148473 A1 and 20030157667 A1).

L-Proline-Producing Bacteria

Examples of L-proline-producing bacteria and parental strains which can be used to derive L-proline-producing bacteria include, but are not limited to, strains belonging to the genus *Escherichia* such as *E. coli* 702ilvA (VKPM B-8012), which is deficient in the ilvA gene and is able to produce L-proline (EP1172433 A1). Examples of L-proline-producing bacteria and parental strains which can be used to derive L-proline-producing bacteria also include strains in which the expression of one or more genes involved in L-proline biosynthesis is enhanced. Examples of such genes which can be used in L-proline-producing bacteria include the proB gene encoding glutamate kinase with desensitized feedback inhibition by L-proline (DE3127361 A1). In addition, examples of L-proline-producing bacteria and parental strains which can be used to derive L-proline-producing bacteria also include strains in which the expression of one or more genes encoding proteins responsible for excreting L-amino acid from the bacterial cell is enhanced. Examples of such genes include the b2682 and b2683 genes (ygaZH genes) (EP1239041 A2).

Examples of bacteria belonging to the genus *Escherichia* that have an ability to produce L-proline include the following *E. coli* strains: NRRL B-12403 and NRRL B-12404 (GB Patent 2075056), VKPM B-8012 (Russian Patent Application No. 2000124295), plasmid mutants described in DE3127361 A1, plasmid mutants described by Bloom F. R. et al. in "The 15$^{th}$ Miami winter symposium", 1983, p. 34, and the like.

L-Threonine-Producing Bacteria

Examples of L-threonine-producing bacteria and parental strains which can be used to derive L-threonine-producing bacteria include, but are not limited to, strains belonging to the genus *Escherichia* such as *E. coli* TDH-6/pVIC40 (VKPM B-3996) (U.S. Pat. Nos. 5,175,107 and 5,705,371), *E. coli* 472T23/pYN7 (ATCC 98081) (U.S. Pat. No. 5,631, 157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner M. et al., Genetika (Russian), 1978, 14:947-956), *E. coli* VL643 and VL2055 (EP1149911 A2), *E. coli* VKPM B-5318 (EP0593792 A1), and the like.

The strain TDH-6 is deficient in the thrC gene, as well as being sucrose-assimilative, and the ilvA gene thereof has a leaky mutation. This strain also has a mutation in the rhtA gene, which mutation imparts resistance to high concentrations of threonine or homoserine. The strain VKPM B-3996, which contains the plasmid pVIC40, was obtained by introducing the plasmid pVIC40 into the TDH-6 strain. The plasmid pVIC40 was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain VKPM B-3996 was deposited on Nov. 19, 1987 in the All-Union Scientific Center of Antibiotics (Russian Federation, 117105 Moscow, Nagatinskaya Street 3-A) under the accession number RIA 1867. The strain VKPM B-3996 was also deposited in the Russian National Collection of Industrial Microorganisms (VKPM) (Russian Federation, 117545 Moscow, 1$^{st}$ Dorozhny proezd, 1) on Apr. 7, 1987 under the accession number VKPM B-3996.

The strain B-5318 is prototrophic with regard to isoleucine; and a temperature-sensitive lambda-phage C1 repressor and PR promoter replace the regulatory region of the threonine operon in plasmid pVIC40. The strain VKPM B-5318 was deposited in the Russian National Collection of Industrial Microorganisms (VKPM) on May 3, 1990 under the accession number VKPM B-5318.

L-threonine-producing bacteria or parental strains which can be used to derive L-threonine-producing bacteria can be additionally modified to enhance expression of one or more of the following genes:

the mutant thrA gene which encodes aspartokinase homoserine dehydrogenase I resistant to feedback inhibition by threonine;
the thrB gene which encodes homoserine kinase;
the thrC gene which encodes threonine synthase;
the rhtA gene which encodes a putative transmembrane protein of the threonine and homoserine efflux system;
the asd gene which encodes aspartate-β-semialdehyde dehydrogenase; and
the aspC gene which encodes aspartate aminotransferase (aspartate transaminase);

The thrA gene which encodes aspartokinase I and homoserine dehydrogenase I of *E. coli* has been elucidated (KEGG, Kyoto Encyclopedia of Genes and Genomes, entry No. b0002; GenBank accession No. NC_000913.2; nucleotide positions: 337 to 2,799; Gene ID: 945803). The thrA gene is located between the thrL and thrB genes on the chromosome of *E. coli* K-12.

The thrB gene which encodes homoserine kinase of *E. coli* has been elucidated (KEGG entry No. b0003; GenBank accession No. NC_000913.2; nucleotide positions: 2,801 to 3,733; Gene ID: 947498). The thrB gene is located between the thrA and thrC genes on the chromosome of *E. coli* K-12.

The thrC gene which encodes threonine synthase of *E. coli* has been elucidated (KEGG entry No. b0004; GenBank accession No. NC_000913.2; nucleotide positions: 3,734 to 5,020; Gene ID: 945198). The thrC gene is located between the thrB and yaaX genes on the chromosome of *E. coli* K-12. All three genes function as a single threonine operon thrABC. To enhance expression of the threonine operon, the attenuator region which affects the transcription is desirably removed from the operon (WO2005049808 A1, WO2003097839 A1).

The mutant thrA gene which encodes aspartokinase I and homoserine dehydrogenase I resistant to feedback inhibition by L-threonine, as well as, the thrB and thrC genes can be obtained as one operon from the well-known plasmid pVIC40 which is present in the L-threonine-producing *E. coli* strain VKPM B-3996. Plasmid pVIC40 is described in detail in U.S. Pat. No. 5,705,371.

The rhtA gene which encodes a protein of the threonine and homoserine efflux system (an inner membrane transporter) of *E. coli* has been elucidated (KEGG entry No. b0813; GenBank accession No. NC_000913.2; nucleotide positions: 848,433 to 849,320, complement; Gene ID: 947045). The rhtA gene is located between the dps and ompX genes on the chromosome of *E. coli* K-12 close to the glnHPQ operon, which encodes components of the glutamine transport system. The rhtA gene is identical to the ybiF gene (KEGG entry No. b0813).

The asd gene which encodes aspartate-β-semialdehyde dehydrogenase of *E. coli* has been elucidated (KEGG entry No. b3433; GenBank accession No. NC_000913.2; nucleotide positions: 3,571,798 to 3,572,901, complement; Gene ID: 947939). The asd gene is located between the glgB and gntU gene on the same strand (yhgN gene on the opposite strand) on the chromosome of *E. coli* K-12.

Also, the aspC gene which encodes aspartate aminotransferase of *E. coli* has been elucidated (KEGG entry No. b0928; GenBank accession No. NC_000913.2; nucleotide positions: 983,742 to 984,932, complement; Gene ID: 945553). The aspC gene is located between the ycbL gene on the opposite strand and the ompF gene on the same strand on the chromosome of *E. coli* K-12.

L-Tryptophan-Producing Bacteria

Examples of L-tryptophan-producing bacteria and parental strains which can be used to derive the L-tryptophan-producing bacteria include, but are not limited to, strains belonging to the genus *Escherichia* such as *E. coli* JP4735/pMU3028 (DSM10122) and JP6015/pMU91 (DSM10123) deficient in the tryptophanyl-tRNA synthetase encoded by mutant trpS gene (U.S. Pat. No. 5,756,345), *E. coli* SV164 (pGH5) having a serA allele encoding phosphoglycerate dehydrogenase free from feedback inhibition by serine and a trpE allele encoding anthranilate synthase free from feedback inhibition by tryptophan (U.S. Pat. No. 6,180,373 B1), *E. coli* AGX17 (pGX44) (NRRL B-12263) and AGX6 (pGX50)aroP (NRRL B-12264) deficient in the enzyme tryptophanase (U.S. Pat. No. 4,371,614), *E. coli* AGX17/pGX50, pACKG4-pps having an enhanced phosphoenolpyruvate-producing ability (WO97/08333, U.S. Pat. No. 6,319,696 B1), and the like. Examples of L-tryptophan-producing bacteria and parental strains which can be used to derive the L-tryptophan-producing bacteria also include strains belonging to the genus *Escherichia* and having an enhanced activity of the protein encoded by and the yedA gene or the yddG gene (U.S. Patent Application Nos. 2003148473 A1 and 2003157667 A1).

Examples of L-tryptophan-producing bacteria and parental strains which can be used to derive the L-tryptophan-producing bacteria also include strains in which one or more activities of the enzymes selected from anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, and hence, a mutation desensitizing the feedback inhibition may be introduced into these enzymes. Specific examples of strains having such a mutation include *E. coli* SV164, which harbors desensitized anthranilate synthase, and a transformant strain obtained by introducing into the *E. coli* SV164 the plasmid pGH5 (WO94/08031 A1), which contains a mutant serA gene encoding feedback-desensitized phosphoglycerate dehydrogenase.

Examples of L-tryptophan-producing bacteria and parental strains which can be used to derive the L-tryptophan-producing bacteria also include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of a and subunits which are encoded by the trpA and trpB genes, respectively. In addition, L-tryptophan-producing ability may be improved by enhancing expression of the isocitrate lyase-malate synthase operon (WO2005/103275).

L-Valine-Producing Bacteria

Examples of L-valine-producing bacteria and parental strains which can be used to derive L-valine-producing bacteria include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by the L-valine that is produced. Furthermore, the ilvA gene in the operon is desirably disrupted so that threonine deaminase activity is decreased.

Examples of L-valine-producing bacteria and parental strains for deriving L-valine-producing bacteria also include mutant strains having a mutation in aminoacyl-tRNA synthetase (U.S. Pat. No. 5,658,766). Examples of such strains include $E.\ coli$ VL1970, which has a mutation in the ileS gene encoding isoleucine tRNA synthetase. $E.\ coli$ VL1970 was deposited in the Russian National Collection of Industrial Microorganisms (VKPM) (Russian Federation, 117545 Moscow, 1$^{st}$ Dorozhny Proezd, 1) on Jun. 24, 1988 under the accession number VKPM B-4411.

Furthermore, mutant strains requiring lipoic acid for growth and/or lacking H$^+$-ATPase can also be used as L-valine-producing bacteria or parental strains (WO96/06926 A1).

Examples of L-valine-producing bacteria and parent strains for deriving L-valine-producing bacteria also include $E.\ coli$ H81 strain (VKPM B-8066; see, for example, EP1942183 B1), $E.\ coli$ NRRL B-12287 and NRRL B-12288 (U.S. Pat. No. 4,391,907), $E.\ coli$ VKPM B-4411 (U.S. Pat. No. 5,658,766), $E.\ coli$ VKPM B-7707 (EP1016710 A2), or the like.

The bacterium of the present invention belonging to the family Enterobacteriaceae has been modified to attenuate expression of a phosphate transporter-encoding gene.

The phrase "a bacterium has been modified to attenuate expression of a phosphate transporter-encoding gene" can mean that the bacterium has been modified in such a way that in the modified bacterium expression of a phosphate transporter-encoding gene is attenuated. For example, the expression of a phosphate transporter-encoding gene can be attenuated due to inactivation of the phosphate transporter-encoding gene.

The phrase "a phosphate transporter-encoding gene is inactivated" can mean that the modified gene encodes a completely inactive or non-functional protein as compared with a bacterium which contains a wild-type or non-modified phosphate transporter-encoding gene. It is also acceptable that the modified DNA region is unable to naturally express the gene due to deletion of a part of the gene or deletion of the entire gene, replacement of one base or more to cause an amino acid substitution in the protein encoded by the gene (missense mutation), introduction of a stop codon (nonsense mutation), deletion of one or two bases to cause a reading frame shift of the gene, insertion of a drug-resistance gene and/or transcription termination signal, or modification of an adjacent region of the gene, including sequences controlling gene expression such as promoter(s), enhancer(s), attenuator(s), ribosome-binding site(s), etc. Inactivation of the gene can also be performed, for example, by conventional methods such as a mutagenesis treatment using UV irradiation or nitrosoguanidine (N-methyl-N'-nitro-N-nitrosoguanidine), site-directed mutagenesis, gene disruption using homologous recombination, and/or insertion-deletion mutagenesis (Yu D. et al., *Proc. Natl. Acad. Sci. USA*, 2000, 97(11):5978-5983; Datsenko K. A. and Wanner B. L., *Proc. Natl. Acad. Sci. USA*, 2000, 97(12): 6640-6645; Zhang Y. et al., *Nature Genet.*, 1998, 20:123-128) based on "Red/ET-driven integration" or "λRed/ET-mediated integration".

The phrase "expression of a phosphate transporter-encoding gene is attenuated" can mean that the amount of a phosphate transporter protein in the modified bacterium, in which expression of the phosphate transporter-encoding gene is attenuated, is reduced as compared with a non-modified bacterium, for example, a wild-type or parental strain such as $E.\ coli$ K-12.

The phrase "expression of a phosphate transporter-encoding gene is attenuated" can also mean that the modified bacterium contains a region operably linked to the gene, including sequences controlling gene expression such as promoters, enhancers, attenuators and transcription termination signals, ribosome-binding sites, and other expression control elements, which is modified resulting in the decrease of the expression level of the phosphate transporter-encoding gene; and other examples (see, for example, WO95/34672; Carrier T. A. and Keasling J. D., *Biotechnol. Prog.*, 1999, 15:58-64). The phrase "operably linked to the gene" can mean that the regulatory region(s) is/are linked to the nucleotide sequence of the nucleic acid molecule or gene in such a manner which allows for expression (e.g., enhanced, increased, constitutive, basal, anti-terminated, attenuated, deregulated, decreased, or repressed expression) of the nucleotide sequence, specifically, the expression of a gene product encoded by the nucleotide sequence.

The phrase "expression of a phosphate transporter-encoding gene is attenuated" can also specifically mean that the expression amount of the phosphate transporter-encoding gene, such as the amount of mRNA of the gene or the amount of the phosphate transporter protein encoded by the gene, is reduced to, for example, 50% or less, 20% or less, 10% or less, 5% or less, or 0% of that of a non-modified bacterium.

Expression of a phosphate transporter-encoding gene can be attenuated by replacing an expression control sequence of the gene, such as a promoter on the chromosomal DNA, with a weaker one. The strength of a promoter is defined by the frequency of initiation acts of RNA synthesis. Examples of methods for evaluating the strength of promoters and strong promoters are described in Goldstein M. A. et al. (Goldstein M. A. and Doi R. H., Prokaryotic promoters in biotechnology, *Biotechnol. Annu. Rev.*, 1995, 1:105-128), and so forth. Furthermore, it is also possible to introduce one or more nucleotide substitutions in a promoter region of the gene and thereby modify the promoter to be weakened as disclosed in WO0018935 A1. Furthermore, it is known that substitution of several nucleotides in the Shine-Dalgarno (SD) sequence, and/or in the spacer between the SD sequence and the start codon, and/or a sequence immediately upstream and/or downstream from the start codon in the ribosome-binding site (RBS) greatly affects the translation efficiency of mRNA. This modification of the RBS may be combined with decreasing transcription of a phosphate transporter-encoding gene.

Expression of a phosphate transporter-encoding gene can also be attenuated by inserting a transposon or an insertion sequence (IS) into the coding region of the gene (U.S. Pat. No. 5,175,107) or in the region controlling gene expression, or by conventional methods such as mutagenesis with ultraviolet (UV) irradiation or nitrosoguanidine (N-methyl-N'-nitro-N-nitrosoguanidine, NTG). Furthermore, the incorporation of a site-specific mutation can be conducted by known chromosomal editing methods based, for example, on XRed/ET-mediated recombination (Datsenko K. A. and Wanner B. L., Proc. Natl. Acad. Sci. USA, 2000, 97(12):6640-6645).

The copy number, presence or absence of the phosphate transporter-encoding gene can be measured, for example, by restricting the chromosomal DNA followed by Southern blotting using a probe based on the gene sequence, fluorescence in situ hybridization (FISH), and the like. The level of gene expression can be determined by measuring the amount of mRNA transcribed from the gene using various well-known methods, including Northern blotting, quantitative RT-PCR, and the like. The amount of the protein encoded by the gene can be measured by known methods including SDS-PAGE followed by immunoblotting assay (Western blotting analysis), or mass spectrometry analysis of the protein samples, and the like.

Methods for manipulation with recombinant molecules of DNA and molecular cloning such as preparation of plasmid DNA, digestion, ligation and transformation of DNA, selection of an oligonucleotide as a primer, incorporation of mutations, and the like may be ordinary methods well-known to the person skilled in the art. These methods are described, for example, in Sambrook J., Fritsch E. F. and Maniatis T., "Molecular Cloning: A Laboratory Manual", $2^{nd}$ ed., Cold Spring Harbor Laboratory Press (1989) or Green M. R. and Sambrook J. R., "Molecular Cloning: A Laboratory Manual", $4^{th}$ ed., Cold Spring Harbor Laboratory Press (2012); Bernard R. Glick, Jack J. Pasternak and Cheryl L. Patten, "Molecular Biotechnology: principles and applications of recombinant DNA", $4^{th}$ ed., Washington, D.C., ASM Press (2009).

The inorganic phosphate-transporting activity of PitA transporter or its homolog or variant protein such as PitB can be determined by evaluating the uptake of inorganic phosphate labeled with radioactive phosphorus-33 ($^{33}$P) (Harris R. M. et al., Characterization of PitA and PitB from Escherichia coli, J. Bacteriol., 2001, 183(17):5008-5014). The protein concentration can be determined by the Bradford protein assay (Bradford M. M., A rapid and sensitive method for the quantitation of microgram quantities of protein utilizing the principle of protein-dye binding, Anal. Biochem., 1976, 72:248-254) using bovine serum albumin as a standard.

The phrase "a phosphate transporter-encoding gene" can mean a gene which encodes a phosphate transporter. The phosphate transporter-encoding gene can be the pitA gene and its homolog(s) or variant nucleotide sequence(s), such as, for example, the pitB gene. The more specific description of pitA, pitB, and its homologs and variant nucleotide sequences is given hereinafter.

The pitA gene (synonym: pit) encodes a low-affinity inorganic phosphate transporter 1 PitA (KEGG, Kyoto Encyclopedia of Genes and Genomes, entry No. b3493; Protein Knowledgebase, UniProtKB/Swiss-Prot, accession No. P0AFJ7). The pitA gene (GenBank accession No. NC_000913.3; nucleotide positions: 3637642 to 3639141; Gene ID: 948009) is located between the yhiN and uspB genes on the opposite strand on the chromosome of E. coli strain K-12. The nucleotide sequence of the pitA gene of E. coli strain K-12 and the amino acid sequence of the PitA protein encoded by the pitA gene of E. coli strain K-12 are shown in SEQ ID NO: 1 and SEQ ID NO: 2, respectively.

The pitB gene encodes a low-affinity inorganic phosphate transporter 2 PitB (KEGG, Kyoto Encyclopedia of Genes and Genomes, entry No. b2987; Protein Knowledgebase, UniProtKB/Swiss-Prot, accession No. P43676). The pitB gene (GenBank accession No. NC_000913.3; nucleotide positions: 3134872 to 3136371, complement; Gene ID: 947475) is located between the yghT gene on the opposite strand and the gss gene on the same strand on the chromosome of E. coli strain K-12. The nucleotide sequence of the pitB gene of E. coli strain K-12 and the amino acid sequence of the PitB protein encoded by the pitB gene of E. coli strain K-12 are shown in SEQ ID NO: 3 and SEQ ID NO: 4, respectively.

Since there may be some differences in DNA sequences between the genera, species, or strains of the family Enterobacteriaceae, the pitA and pitB genes are not limited to the genes shown in SEQ ID NOs: 1 and 3, but may include genes which are variant nucleotide sequences of or homologous to SEQ ID NO: 1 or 3, and which encode variant PitA and PitB proteins.

The phrase "a variant protein" can mean a protein which has one or several changes in the sequence compared with SEQ ID NO: 2 or 4, whether they are substitutions, deletions, insertions, and/or additions of one or several amino acid residues, but still maintains an activity or function similar to that of the PitA or PitB protein, or the three-dimensional structure of the PitA or PitB protein is not significantly changed relative to the wild-type or non-modified protein. The number of changes in the variant protein depends on the position of amino acid residues in the three-dimensional structure of the protein or the type of amino acid residues. It can be, but is not strictly limited to, 1 to 30, in another example 1 to 15, in another example 1 to 10, and in another example 1 to 5, in SEQ ID NO: 2 or 4. This is because some amino acids have high homology to one another so that the activity or function is not affected by such a change, or the three-dimensional structure of PitA or PitB is not significantly changed relative to the wild-type or non-modified protein. Therefore, the protein variants encoded by the pitA and pitB genes may have a homology, defined as the parameter "identity" when using the computer program BLAST, of not less than 80%, not less than 85%, not less than 90%, not less than 95%, not less than 98%, or not less than 99% with respect to the entire amino acid sequence shown in SEQ ID NO: 2 or 4, as long as the activity or function of the PitA or PitB protein is maintained, or the three-dimensional structure of PitA or PitB is not significantly changed relative to the wild-type or non-modified protein.

The exemplary substitution, deletion, insertion, and/or addition of one or several amino acid residues can be a conservative mutation(s). The representative conservative mutation is a conservative substitution. The conservative substitution can be, but is not limited to, a substitution, wherein substitution takes place mutually among Phe, Trp and Tyr, if the substitution site is an aromatic amino acid; among Ala, Leu, Ile and Val, if the substitution site is a hydrophobic amino acid; between Glu, Asp, Gln, Asn, Ser, His and Thr, if the substitution site is a hydrophilic amino acid; between Gln and Asn, if the substitution site is a polar amino acid; among Lys, Arg and His, if the substitution site is a basic amino acid; between Asp and Glu, if the substitution site is an acidic amino acid; and between Ser and Thr, if the substitution site is an amino acid having hydroxyl group. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

The exemplary substitution, deletion, insertion, and/or addition of one or several amino acid residues can also be a non-conservative mutation(s) provided that the mutation(s) is/are compensated by one or more secondary mutations in the different position(s) of amino acids sequence so that the activity or function of the variant protein is maintained and similar to that of the PitA or PitB protein, or the three-dimensional structure of PitA or PitB is not significantly changed relative to the wild-type or non-modified protein.

To evaluate the degree of protein or DNA homology, several calculation methods can be used, such as BLAST search, FASTA search and ClustalW method. The BLAST (Basic Local Alignment Search Tool, ncbi.nlm.nih.gov/BLAST/) search is the heuristic search algorithm employed by the programs blastp, blastn, blastx, megablast, tblastn, and tblastx; these programs ascribe significance to their findings using the statistical methods of Karlin S. et al. (Karlin S. and Altschul S. F., Methods for assessing the statistical significance of molecular sequence features by using general scoring schemes, *Proc. Natl. Acad. Sci. USA,* 1990, 87:2264-2268; Karlin S. and Altschul S. F., Applications and statistics for multiple high-scoring segments in molecular sequences, *Proc. Natl. Acad. Sci. USA,* 1993, 90:5873-5877). The computer program BLAST calculates three parameters: score, identity and similarity. The FASTA search method is described in Pearson W. R. (Rapid and sensitive sequence comparison with FASTP and FASTA, *Methods Enzymol.,* 1990, 183:63-98). The ClustalW method is also described in Thompson J. D. et al. (CLUSTAL W: improving the sensitivity of progressive multiple sequence alignment through sequence weighting, position-specific gap penalties and weight matrix choice, *Nucleic Acids Res.,* 1994, 22:4673-4680).

Moreover, the pitA and pitB genes can be variant nucleotide sequences. The phrase "a variant nucleotide sequence" can mean a nucleotide sequence which encodes "a variant protein" using any synonymous amino acid codons according to the standard genetic code table (see, e.g., Lewin B., "Genes VIII", 2004, Pearson Education, Inc., Upper Saddle River, N.J. 07458). Therefore, the pitA and pitB genes can be variant nucleotide sequences due to the degeneracy of the genetic code.

The phrase "a variant nucleotide sequence" can also mean, but is not limited to, a nucleotide sequence which hybridizes under stringent conditions with the nucleotide sequence complementary to the sequence shown in SEQ ID NO: 1 or 3, or a probe which can be prepared from the nucleotide sequence under stringent conditions provided that it encodes functional protein. "Stringent conditions" include those under which a specific hybrid, for example, a hybrid having homology, defined as the parameter "identity" when using the computer program BLAST, of not less than 75%, not less than 80%, not less than 85%, not less than 90%, not less than 95%, not less than 96%, not less than 97%, not less than 98%, or not less than 99% is formed, and a non-specific hybrid, for example, a hybrid having homology lower than the above is not formed. For example, stringent conditions can be exemplified by washing one time or more, or in another example, two or three times, at a salt concentration of 1×SSC (standard sodium citrate or standard sodium chloride), 0.1% SDS (sodium dodecyl sulphate), or in another example, 0.1×SSC, 0.1% SDS at 60° C. or 65° C. Duration of washing depends on the type of membrane used for blotting and, as a rule, can be what is recommended by the manufacturer. For example, the recommended duration of washing for the Amersham Hybond™-N+ positively charged nylon membrane (GE Healthcare) under stringent conditions is 15 minutes. The washing step can be performed 2 to 3 times. As the probe, a part of the sequence complementary to the sequences shown in SEQ ID NO: 1 or 3 may also be used. Such a probe can be produced by PCR using oligonucleotides as primers prepared on the basis of the sequence shown in SEQ ID NO: 1 or 3 and a DNA fragment containing the nucleotide sequence as a template. The length of the probe is recommended to be >50 bp; it can be suitably selected depending on the hybridization conditions, and is usually 100 bp to 1 kbp. For example, when a DNA fragment having a length of about 300 bp is used as the probe, the washing conditions after hybridization can be exemplified by 2×SSC, 0.1% SDS at 50° C., 60° C. or 65° C.

As the genes encoding the PitA and PitB proteins of the species *E. coli* have already been elucidated (see above), the variant nucleotide sequences encoding variant proteins of PitA and PitB proteins can be obtained by PCR (polymerase chain reaction; refer to White T. J. et al., The polymerase chain reaction, *Trends Genet.,* 1989, 5:185-189) utilizing primers prepared based on the nucleotide sequence of the pitA or pitB gene; or the site-directed mutagenesis method by treating a DNA containing the wild-type pitA or pitB gene in vitro, for example, with hydroxylamine, or a method for treating a microorganism, for example, a bacterium belonging to the family Enterobacteriaceae harboring the wild-type pitA and pitB genes with ultraviolet (UV) irradiation or a mutating agent such as N-methyl-N'-nitro-N-nitrosoguanidine (NTG) and nitrous acid usually used for the such treatment; or chemically synthesized as full-length gene structure. Genes encoding the PitA and PitB proteins or its variant proteins of other microorganisms can be obtained in a similar manner.

The phrase "a wild-type protein" can mean a native protein naturally produced by a wild-type or non-modified bacterial strain of the family Enterobacteriaceae, for example, by the wild-type *E. coli* MG1655 strain. A wild-type protein can be encoded by the wild-type, or non-modified, gene naturally occurring in the genome of a wild-type bacterium.

The bacterium as described herein can be obtained by modifying a bacterium inherently having an ability to produce an L-amino acid to attenuate expression of a phosphate transporter-encoding gene. Alternatively, the bacterium as described herein can be obtained by imparting the ability to produce an L-amino acid to a bacterium already modified to attenuate expression of the phosphate transporter-encoding gene.

The above descriptions concerning variants of the genes and proteins can also be applied mutatis mutandis to arbitrary proteins such as L-amino acid biosynthesis enzymes and genes coding for them.

The bacterium can have, in addition to the properties already mentioned, other specific properties such as various nutrient requirements, drug resistance, drug sensitivity, and drug dependence, without departing from the scope of the present invention.

2. Method

The method of the present invention includes a method for producing an L-amino acid such as L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine, or a salt thereof, or a mixture thereof. Specifically, the method of the present invention includes the method for producing L-arginine, L-glutamine, L-histidine, and L-proline, or a mixture thereof. More specifically, the method of the present invention includes the method for producing L-arginine and L-histidine.

The method for producing an L-amino acid can include the steps of cultivating the bacterium as described herein in a culture medium to allow the L-amino acid to be produced, excreted, and/or accumulated in the culture medium or in the bacterial cells, and collecting the L-amino acid from the culture medium and/or the bacterial cells. Collected amino acid can be further purified. The L-amino acid can be produced in a free form, a salt form or a hydrate form thereof, or an adduct form thereof with another organic or inorganic compound, or as a combination thereof. For example, sodium, potassium, ammonium, and the like salts of the L-amino acid can be produced by the method. Specifically, a monochlorhydrate salt of an L-amino acid can be produced by the method such as monochlorhydrate salt of L-lysine (L-lysine-HCl) or monochlorhydrate salt of L-arginine (L-arginine-HCl); or monochlorhydrate salt monohydrate of an L-amino acid can be produced by the method such as monochlorhydrate monohydrate of L-histidine (L-histidine-HCl.H$_2$O).

The cultivation of the bacterium, and collection and purification of L-amino acid may be performed in a manner similar to conventional fermentation methods wherein L-amino acid is produced using a microorganism. The culture medium for production of the L-amino acid can be either a synthetic or natural medium such as a typical medium that contains a carbon source, a nitrogen source, a sulphur source, inorganic ions, and other organic and inorganic components as required. As the carbon source, saccharides such as glucose, lactose, galactose, fructose, arabinose, maltose, xylose, trehalose, ribose, sucrose, and hydrolysates of starches; alcohols such as ethanol, glycerol, mannitol, and sorbitol; organic acids such as gluconic acid, fumaric acid, citric acid, malic acid, and succinic acid; fatty acids; and the like can be used. As the nitrogen source, inorganic ammonium salts such as ammonium sulfate, ammonium chloride, and ammonium phosphate; organic nitrogen such as of soy bean hydrolyzates; ammonia gas; aqueous ammonia; and the like can be used. The sulphur source can include ammonium sulphate, magnesium sulphate, ferrous sulphate, manganese sulphate, and the like. The medium can contain a phosphorus source in addition to a carbon source, a nitrogen source, and a sulphur source. As the phosphorus source, potassium dihydrogen phosphate, dipotassium hydrogen phosphate, phosphate polymers such as pyrophosphoric acid and so forth can be utilized. Vitamins such as vitamin B1, vitamin B2, vitamin B6, nicotinic acid, nicotinamide, and vitamin B12; required substances, for example, organic nutrients such as nucleic acids such as adenine and RNA, or yeast extract; and the like may be present in appropriate, even if trace, amounts. Other than these, small amounts of calcium phosphate, iron ions, manganese ions, and the like may be added, if necessary.

Cultivation can be performed under aerobic conditions for 16 to 72 h, or for 16 to 65 h; the culture temperature during cultivation can be controlled within 30 to 45° C., or within 30 to 37° C.; and the pH can be adjusted between 5 and 8, or between 6.0 and 7.5. The pH can be adjusted by using an inorganic or organic acidic or alkaline substance, as well as ammonia gas.

After cultivation, solids such as cells and cell debris can be removed from the liquid medium by centrifugation or membrane filtration, and then the target L-amino acid can be recovered from the fermentation liquor by any combination of conventional techniques such as concentration, ion-exchange chromatography, and crystallization.

The collected target L-amino acid composition may contain microbial cells, medium components, moisture, and by-product metabolites of the microorganism in addition to the target L-amino acid. Purity of the collected target substance is 50% or higher, preferably 85% or higher, particularly preferably 95% or higher (U.S. Pat. No. 5,431,933, Japanese Patent No. 1214636, U.S. Pat. Nos. 4,956,471, 4,777,051, 4,946,654, 5,840,358, 6,238,714, U.S. Patent Published Application No. 2005/0025878).

EXAMPLES

The present invention will be more specifically explained below with reference to the following non-limiting examples.

Example 1. Construction of the *E. coli* L-Histidine-Producing Strain Having an Inactivated pitA Gene a. Construction of *E. coli* MG1655ΔpitA Strain An *E. coli* strain having an inactivated pitA gene was constructed by the method initially developed by Datsenko K. A. and Wanner B. L. called "λRed/ET-mediated integration" (Datsenko K. A. and Wanner B. L., *Proc. Natl. Acad. Sci. USA*, 2000, 97(12):6640-6645). A DNA-fragment containing the kanamycin resistance marker (Km$^R$) was obtained by PCR using primers P1 (SEQ ID NO: 5) and P2 (SEQ ID NO: 6), and the pMW118-λattL-Km$^R$-λattR plasmid (WO2011043485 A1) as the template (FIG. 1). The pMW118-λattL-Km$^R$-λattR plasmid was constructed from the pMW118-attL-Tc$^R$-attR plasmid (WO2005/010175) by substituting the tetracycline resistance marker gene thereof with the kanamycin resistance marker gene (kan) from pUC4K plasmid (Vieira J. and Messing J., *Gene*, 1982, 19(3):259-268). Primers P1 and P2 are homologous to both regions adjacent to the pitA gene and the kan gene conferring kanamycin resistance in the template plasmid. Conditions for PCR were as follows: denaturation for 3 min at 95° C.; profile for the initial 2 cycles: 1 min at 95° C., 30 sec at 34° C., 40 sec at 72° C.; profile for the final 30 cycles: 30 sec at 95° C., 30 sec at 50° C., 40 sec at 72° C.; final elongation: 5 min at 72° C.

The obtained PCR-product 1 (SEQ ID NO: 7; 1,613 bp) was purified by electrophoresis in agarose gel and used for electroporation of the *E. coli* MG1655 strain containing the pKD46 plasmid having a temperature-sensitive replication origin. The pKD46 plasmid (Datsenko K. A. and Wanner B. L., *Proc. Natl. Acad. Sci. USA*, 2000, 97(12):6640-6645) includes a 2,154 nucleotides DNA-fragment of phage λ (nucleotide positions from 31088 to 33241, GenBank accession No.: J02459), and contains genes of the λRed homologous recombination system (γ, β, and exo genes) under the control of the arabinose-inducible $P_{araB}$ promoter. The pKD46 plasmid is necessary for integration of the PCR-product into the chromosome of the *E. coli* MG1655 strain (ATCC 47076). The *E. coli* MG1655 strain containing the plasmid pKD46 can be obtained from the *E. coli* Genetic Stock Center, Yale University, New Haven, USA (Accession No. CGSC7669).

Electrocompetent cells were prepared as follows: *E. coli* MG1655/pKD46 was grown overnight at 30° C. in LB-medium (Luria-Bertani broth, also referred to as lysogenic broth; Sambrook J. and Russell D. W., Molecular Cloning: A Laboratory Manual (3$^{rd}$ ed.), Cold Spring Harbor Laboratory Press, 2001) containing ampicillin (100 mg/L); then the culture was diluted 100 times with 5 mL of SOB-medium (Sambrook J. et al., Molecular Cloning: A Laboratory Manual (2$^{nd}$ ed.), Cold Spring Harbor Laboratory Press, 1989) containing ampicillin (100 mg/L) and L-arabinose (1 mM); the obtained culture was grown with aeration (250 rpm) at 30° C. to $OD_{600}$ of about 0.6 and then made electrocompetent by concentrating 100-fold and washing three times with ice-cold deionized $H_2O$. Electroporation was performed using 70 μL of cells and about 100 ng of the PCR-product. Electroporated cells were incubated with 1 mL of SOC-medium (Sambrook J. et al., Molecular Cloning: A Laboratory Manual (2$^{nd}$ ed.), Cold Spring Harbor Laboratory Press, 1989) at 37° C. for 2.5 h, placed onto the plates containing the lysogenic broth (Sambrook J. and Russell D. W., Molecular Cloning: A Laboratory Manual (3$^{rd}$ ed.), Cold Spring Harbor Laboratory Press, 2001), agar (1.5%) and kanamycin (50 mg/L), and grown at 37° C. to select Km$^R$-recombinants. To eliminate the pKD46 plasmid, two passages on L-agar supplemented with kanamycin (50 mg/L) at 42° C. were performed, and the obtained colonies were tested for sensitivity to ampicillin. Thus the *E. coli* MG1655ΔpitA strain having the Km$^R$-marker was obtained.

1.2. Verification of Deletion of the pitA Gene

The deletion of pitA gene marked with kanamycin resistance gene in the mutant *E. coli* MG1655ΔpitA strain was verified by PCR. Locus-specific primers P3 (SEQ ID NO: 8) and P4 (SEQ ID NO: 9) were used for the verification. Conditions for PCR were as follows: denaturation for 3 min at 94° C.; profile for the 30 cycles: 30 sec at 94° C., 30 sec at 55° C., 2 min at 72° C.; final elongation: 6 min at 72° C. The PCR-product 2, obtained in the reaction with the chromosomal DNA as the template from the parental *E. coli* MG1655 having native pitA gene, was 1,599 bp in length (SEQ ID NO: 10). The PCR-product 3, obtained in the reaction with the chromosomal DNA as a template from the mutant *E. coli* MG1655ΔpitA strain having the Km$^R$-marker, was 1,670 bp in length (SEQ ID NO: 11).

Example 2. Production of L-Histidine by *E. coli* MG1655+hisGr hisL'_Δ ΔpurR ΔpitA strain To test the effect from inactivation of the pitA gene on L-histidine production, the DNA-fragments from the chromosome of the above-described *E. coli* MG1655ΔpitA strain (Example 1) were transferred to the histidine-producing *E. coli* strain MG1655+hisGr hisL'_Δ ΔpurR by P1-transduction (Miller, J. H. (1972) <<Experiments in Molecular Genetics>>, Cold Spring Harbor Lab. Press, Plainview, N.Y.) to obtain the strain MG1655+hisGr hisL'_Δ ΔpurR ΔpitA having the Km$^R$-marker. The *E. coli* strain MG1655+hisGr hisL'_Δ ΔpurR is described in Doroshenko V. G. et al., The directed modification of *Escherichia coli* MG1655 to obtain histidine-producing mutants, *Prikl. Biokhim. Mikrobiol.* (in Russian), 2013, 49(2):149-154. The deletion of pitA marked with kanamycin resistance gene was verified by PCR as described in Example 1.2.

*E. coli* strains MG1655+hisGr hisL'_Δ ΔpurR and MG1655+hisGr hisL'_Δ ΔpurR ΔpitA were separately cultivated in 2 mL of LB-medium for 3 h at 30° C. Then, 0.1 mL of obtained cultures were each inoculated into 2 mL of fermentation medium in 20×200-mm test tubes and cultivated for 65 h at 30° C. with shaking on a rotary shaker (250 rpm) until glucose consumption.

The composition of the fermentation medium (g/L) was as follows:

| | |
|---|---|
| Glucose | 25.0 |
| Mameno* | 0.1 (as the amount of nitrogen) |
| L-Aspartate | 0.5 |
| $(NH_4)_2SO_4$ | 9.0 |
| KCl | 0.5 |
| $KH_2PO_4$ | 0.25 |
| $MgSO_4 \cdot 7H_2O$ | 0.2 |
| $FeSO_4 \cdot 7H_2O$ | 0.01 |
| $MnSO_4 \cdot 5H_2O$ | 0.01 |
| $ZnSO_4 \cdot 7H_2O$ | 0.01 |
| Adenosine | 0.1 |
| Thiamine-HCl | 0.0005 |
| Betaine | 1.0 |
| $CaCO_3$ | 30.0 |

*Mameno is the soybean meal hydrolysate (Ajinomoto Co., Inc.).

Glucose, magnesium sulfate, betaine, and $CaCO_3$ were sterilized separately. The pH was adjusted to 6.0 by 6 M KOH before sterilization.

After cultivation, the amount of L-histidine, which accumulated in the medium, was determined by thin layer chromatography (TLC). The 10×20-cm TLC plates coated with 0.11-mm layers of Sorbfil silica gel containing non-fluorescent indicator (Stock Company Sorbpolymer, Krasnodar, Russian Federation) were used. Samples were applied onto the plates using the Camag Linomat 5 sample applicator. The Sorbfil plates were developed with a mobile phase consisting of propan-2-ol:acetone:25% aqueous ammonia: water=6:6:1.5:1 (v/v). A solution of ninhydrin (1%, w/v) in acetone was used as a visualizing reagent. After development, plates were dried and scanned with the Camag TLC Scanner 3 in absorbance mode with detection at 520 nm using winCATS software (version 1.4.2).

The results of seven independent test-tube fermentations (as average values) are shown in Table 1. As it can be seen from the Table 1, the modified *E. coli* MG1655+hisGr hisL'_Δ ΔpurR ΔpitA strain was able to produce a higher amount of L-histidine (His) as compared with the parent *E. coli* MG1655+hisGr hisL'_Δ ΔpurR strain.

TABLE 1

Production of L-histidine.

| Strain | $OD_{550}$ | His, g/L |
|---|---|---|
| *E. coli* MG1655+hisGr hisL'_Δ ΔpurR (control) | 14.9 | 3.4 |
| *E. coli* MG1655+hisGr hisL'_Δ ΔpurR ΔpitA | 11.3 | 3.8 |

Example 3. Production of L-Arginine by E. coli 382 ilvA+ΔpitA Strain

The E. coli strain 382 ilvA+ was obtained from the arginine-producing E. coli strain 382 (VKPM B-7926, EP1170358 A1) by introducing the wild-type allele of ilvA gene from E. coli K-12 strain by P1-transduction (Miller, J. H. (1972) <<Experiments in Molecular Genetics>>, Cold Spring Harbor Lab. Press, Plainview, N.Y.). The E. coli strain 382 was deposited in the Russian National Collection of Industrial Microorganisms (VKPM) (Russian Federation, 117545 Moscow, 1$^{st}$ Dorozhny proezd, 1) on Apr. 10, 2000 under the accession number VKPM B-7926 and then converted to a deposit under the Budapest Treaty on May 18, 2001.

To test the effect from inactivation of the pitA gene on L-arginine production, the DNA-fragments from the chromosome of the above-described E. coli MG1655ΔpitA strain were transferred to the arginine-producing E. coli strain 382 ilvA+ by P1-transduction to obtain the strain 382 ilvA+ ΔpitA having the Km$^R$-marker.

E. coli strains 382 ilvA+ and 382 ilvA+ΔpitA were separately cultivated with shaking (220 rpm) at 32° C. for 5 h in 2 mL of the LB-medium. Then, 0.3 mL of the obtained cultures were each inoculated into 2 mL of a fermentation medium in 20×200-mm test tubes and cultivated at 32° C. for 72 h on a rotary shaker (220 rpm).

After cultivation, the amount of L-arginine, which accumulated in the medium, was determined by thin layer chromatography (TLC). The 10×20-cm TLC plates coated with 0.11-mm layers of Sorbfil silica gel (Stock Company Sorbpolymer, Krasnodar, Russian Federation) were used. Samples were applied onto the plates using the Camag Linomat 5 sample applicator. The Sorbfil plates were developed with a mobile phase consisting of propan-2-ol:ethyl acetate:25% aqueous ammonia:water=4:2:1.25:2.5 (v/v). A solution of ninhydrin (1%) in acetone was used as a visualizing reagent. After development, plates were dried and scanned with the Camag TLC Scanner 3 in absorbance mode with detection at 520 nm using winCATS software (version 1.4.2).

The composition of the fermentation medium (g/L) was as follows:

| | |
|---|---|
| Glucose | 48.0 |
| (NH$_4$)$_2$SO$_4$ | 35.0 |
| KH$_2$PO$_4$ | 2.0 |
| MgSO$_4$·7H$_2$O | 1.0 |
| Thiamine-HCl | 0.0002 |
| Yeast extract | 1.0 |
| CaCO$_3$ | 5.0 |

Glucose and magnesium sulfate were sterilized separately. CaCO$_3$ was dry-heat sterilized at 180° C. for 2 h. The pH was adjusted to 7.0.

The results of six independent test-tube fermentations (as average values) are shown in Table 2. As it can be seen from the Table 2, the modified E. coli 382 ilvA+ΔpitA strain was able to produce a higher amount of L-arginine (Arg) as compared with the parent E. coli 382 ilvA+ strain.

TABLE 2

Production of L-arginine.

| Strain | OD$_{550}$ | Arg, g/L |
|---|---|---|
| E. coli 382 ilvA+ (control) | 19.3 | 6.1 |
| E. coli 382 ilvA+ ΔpitA | 18.0 | 6.3 |

Example 4. Production of L-Citrulline by E. coli 382ΔargG ΔpitA

To test the effect from inactivation of the pitA gene on L-citrulline production, the DNA-fragments from the chromosome of the above-described E. coli MG1655ΔpitA strain are transferred to the citrulline-producing E. coli strain 382ΔargG by P1-transduction to obtain the strain 382ΔargG ΔpitA. The strain 382ΔargG is obtained by deletion of argG gene on the chromosome of the arginine-producing strain 382 (VKPM B-7926, EP1170358 A1) by the method initially developed by Datsenko K. A. and Wanner B. L. called "λRed/ET-mediated integration" (Datsenko K. A. and Wanner B. L., Proc. Natl. Acad. Sci. USA, 2000, 97(12):6640-6645). According to this procedure, the PCR-primers homologous to both the region adjacent to the argG gene and the gene which confers antibiotic resistance in the template plasmid are constructed. The plasmid pMW118-λattL-cat-λattR (WO05/010175) is used as the template in the PCR reaction.

E. coli strains 382ΔargG and 382ΔargG ΔpitA are separately cultivated with shaking at 37° C. for 18 h in 3 mL of nutrient broth, and 0.3 mL of the obtained cultures are each inoculated into 2 mL of a fermentation medium in 20×200-mm test tubes and cultivated at 32° C. for 48 h on a rotary shaker.

After the cultivation, the amount of L-citrulline, which accumulates in the medium, is determined by paper chromatography using a mobile phase consisting of butan-1-ol: acetic acid:water=4:1:1 (v/v). A solution of ninhydrin (2%) in acetone is used as a visualizing reagent. A spot containing citrulline is cut out, L-citrulline is eluted with 0.5% water solution of CdCl$_2$, and the amount of L-citrulline is estimated spectrophotometrically at 540 nm.

The composition of the fermentation medium (g/L) is as follows:

| | |
|---|---|
| Glucose | 48.0 |
| (NH$_4$)$_2$SO$_4$ | 35.0 |
| KH$_2$PO$_4$ | 2.0 |
| MgSO$_4$·7H$_2$O | 1.0 |
| Thiamine-HCl | 0.0002 |
| Yeast extract | 1.0 |
| L-Isoleucine | 0.1 |
| L-Arginine | 0.1 |
| CaCO$_3$ | 5.0 |

Glucose and magnesium sulfate are sterilized separately. CaCO$_3$ is dry-heat sterilized at 180° C. for 2 h. The pH is adjusted to 7.0.

Example 5. Production of L-Cysteine by E. coli JM15(ydeD)ΔpitA

To test the effect from inactivation of the pitA gene on L-cysteine production, the DNA fragments from the chromosome of the above-described E. coli MG1655ΔpitA strain are transferred to the cysteine-producing E. coli strain JM15 (ydeD) by P1-transduction to obtain the strain JM15(ydeD) ΔpitA. E. coli JM15(ydeD) is a derivative of E. coli JM15 (CGSC#5042) (U.S. Pat. No. 6,218,168 B1), which is transformed with DNA containing the ydeD gene (U.S. Pat. No. 5,972,663). The ydeD gene encodes a membrane protein, and is not involved in a biosynthetic pathway of any L-amino acid.

Fermentation conditions and procedure for evaluation of L-cysteine production were described in detail in Example 6 of U.S. Pat. No. 6,218,168 B1.

Example 6. Production of L-Glutamic Acid by *E. coli* VL334thrC⁺ΔpitA

To test the effect from inactivation of the pitA gene on L-glutamic acid production, the DNA fragments from the chromosome of the above-described *E. coli* MG1655ΔpitA strain are transferred to the glutamate-producing *E. coli* strain VL334thrC⁺ (EP1172433 A1) by P1-transduction to obtain the strain VL334thrC⁺ΔpitA. The strain VL334thrC⁺ was deposited in the Russian National Collection of Industrial Microorganisms (VKPM) (Russian Federation, 117545 Moscow, 1 Dorozhny proezd, 1) on Dec. 6, 2004 under the accession number VKPM B-8961, and then converted to a deposit under the Budapest Treaty on Dec. 8, 2004.

*E. coli* strains VL334thrC⁺ and VL334thrC⁺ΔpitA are separately cultivated for 18-24 h at 37° C. on L-agar plates. Then, one loop of the cells is transferred into 20×200-mm test tubes containing 2 mL of fermentation medium. Cultivation is carried out at 30° C. for 3 days with shaking.

After the cultivation, the amount of L-glutamic acid which accumulates in the medium is determined by paper chromatography using a mobile phase consisting of butan-1-ol:acetic acid:water=4:1:1 (v/v) with subsequent staining by ninhydrin (1% solution in acetone), elution of L-glutamic acid in 50% ethanol with 0.5% $CdCl_2$ and further estimation of the amount of L-glutamic acid at 540 nm.

The composition of the fermentation medium (g/L) is as follows:

| | |
|---|---|
| Glucose | 60.0 |
| $(NH_4)_2SO_4$ | 25.0 |
| $KH_2PO_4$ | 2.0 |
| $MgSO_4 \cdot 7H_2O$ | 1.0 |
| Thiamine-HCl | 0.1 |
| L-Isoleucine | 0.07 |
| $CaCO_3$ | 25.0 |

Glucose and $CaCO_3$ are sterilized separately. The pH is adjusted to 7.2.

Example 7. Production of L-Leucine by *E. coli* 57ΔpitA

To test the effect from inactivation of the pitA gene on L-leucine production, the DNA fragments from the chromosome of the above-described *E. coli* MG1655ΔpitA strain are transferred to the leucine-producing *E. coli* strain 57 (VKPM B-7386, U.S. Pat. No. 6,124,121) by P1-transduction to obtain the strain 57ΔpitA. The strain 57 was deposited in the Russian National Collection of Industrial Microorganisms (VKPM) (Russian Federation, 117545 Moscow, 1ˢᵗ Dorozhny proezd, 1) on May 19, 1997 under the accession number VKPM B-7386.

*E. coli* strains 57 and 57ΔpitA are separately cultivated for 18-24 h at 37° C. on L-agar plates. To obtain a seed culture, the strains are grown on a rotary shaker (250 rpm) at 32° C. for 18 h in 20×200-mm test tubes containing 2 mL of L-broth (Sambrook, J. and Russell, D. W. (2001) "Molecular Cloning: A Laboratory Manual", 3ʳᵈ ed., Cold Spring Harbor Laboratory Press) supplemented with sucrose (4%). Then, the fermentation medium is inoculated with 0.2 mL of seed material (10%). The fermentation is performed in 2 mL of a minimal fermentation medium in 20×200-mm test tubes. Cells are grown for 48-72 h at 32° C. with shaking at 250 rpm.

After the cultivation, the amount of L-leucine which accumulates in the medium is determined by paper chromatography using a mobile phase consisting of butan-1-ol:acetic acid:water=4:1:1 (v/v).

The composition of the fermentation medium (g/L) is as follows:

| | |
|---|---|
| Glucose | 60.0 |
| $(NH_4)_2SO_4$ | 25.0 |
| $K_2HPO_4$ | 2.0 |
| $MgSO_4 \cdot 7H_2O$ | 1.0 |
| Thiamine-HCl | 0.01 |
| $CaCO_3$ | 25.0 |

Glucose is sterilized separately. $CaCO_3$ is dry-heat sterilized at 180° C. for 2 h. The pH is adjusted to 7.2.

Example 8. Production of L-lysine by *E. coli* AJ11442ΔpitA

To test the effect from inactivation of the pitA gene on L-lysine production, the DNA fragments from the chromosome of the above-described *E. coli* MG1655ΔpitA strain are transferred to the lysine-producing *E. coli* strain AJ11442 by P1-transduction to obtain the AJ11442ΔpitA strain. The strain AJ11442 was deposited in National Institute of Bioscience and Human Technology of Agency of Industrial Science and Technology (currently NITE IPOD, #120, 2-5-8 Kazusakamatari, Kisarazu-shi, Chiba-ken, 292-0818, Japan) on May 1, 1981 under the deposition number FERM P-5084, and received an accession number of FERM BP-1543. The pCABD2 plasmid includes the dapA gene encoding dihydrodipicolinate synthase having a mutation which desensitizes feedback inhibition by L-lysine, the lysC gene encoding aspartokinase III having a mutation which desensitizes feedback inhibition by L-lysine, the dapB gene encoding dihydrodipicolinate reductase, and the ddh gene encoding diaminopimelate dehydrogenase (U.S. Pat. No. 6,040,160).

*E. coli* strains AJ11442 and AJ11442ΔpitA are separately cultivated in L-medium containing streptomycin (20 mg/L) at 37° C., and 0.3 mL of the obtained cultures are each inoculated into 20 mL of the fermentation medium containing the required drugs in a 500-mL flask. The cultivation is carried out at 37° C. for 16 h by using a reciprocal shaker at the agitation speed of 115 rpm.

After the cultivation, the amounts of L-lysine and residual glucose in the medium are determined by a known method (Biotech-analyzer AS210, Sakura Seiki Co.). Then, the yield of L-lysine is calculated relative to consumed glucose for each of the strains.

The composition of the fermentation medium (g/L) is as follows:

| | |
|---|---|
| Glucose | 40.0 |
| $(NH_4)_2SO_4$ | 24.0 |
| $K_2HPO_4$ | 1.0 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Yeast extract | 2.0 |

The pH is adjusted to 7.0 by KOH and the medium is autoclaved at 115° C. for 10 min. Glucose and magnesium sulfate are sterilized separately. CaCO₃ is dry-heat sterilized at 180° C. for 2 h and added to the medium for a final concentration of 30 g/L.

Example 9. Production of L-Ornithine by E. coli 382ΔargFΔargI, ΔpitA

To test the effect from inactivation of the pitA gene on L-ornithine production, the DNA-fragments from the chromosome of the above-described E. coli MG1655ΔpitA strain are transferred to the ornithine-producing E. coli strain 382ΔargFΔargI by P1-transduction to obtain the strain 382ΔargFΔargI,ΔpitA. The strain 382ΔargFΔargI is obtained by consecutive deletion of argF and argI genes on the chromosome of the L-arginine-producing strain 382 (VKPM B-7926, EP1170358 A1) by the method initially developed by Datsenko K. A. and Wanner B. L. called "λRed/ET-mediated integration" (Datsenko K. A. and Wanner B. L., *Proc. Natl. Acad. Sci. USA*, 2000, 97(12):6640-6645). According to this procedure, two pairs of PCR-primers homologous to both the region adjacent to the argF or argI gene and the gene which confers antibiotic resistance in the template plasmid are constructed. The plasmid pMW118-λattL-cat-λattR (WO05/010175) is used as the template in the PCR reaction.

E. coli strains 382ΔargFΔargI and 382ΔargFΔargI,ΔpitA are separately cultivated with shaking at 37° C. for 18 h in 3 mL of nutrient broth, and 0.3 mL of the obtained cultures are each inoculated into 2 mL of a fermentation medium in 20×200-mm test tubes and cultivated at 32° C. for 48 h on a rotary shaker.

After the cultivation, the amount of L-ornithine which accumulates in the medium is determined by paper chromatography using a mobile phase consisting of butan-1-ol:acetic acid:water=4:1:1 (v/v). A solution of ninhydrin (2%) in acetone is used as a visualizing reagent. A spot containing ornithine is cut out, ornithine is eluted with 0.5% water solution of CdCl₂, and the amount of ornithine is estimated spectrophotometrically at 540 nm.

The composition of the fermentation medium (g/L) is as follows:

| | |
|---|---|
| Glucose | 48.0 |
| (NH₄)₂SO₄ | 35.0 |
| KH₂PO₄ | 2.0 |
| MgSO₄•7H₂O | 1.0 |
| Thiamine-HCl | 0.0002 |
| Yeast extract | 1.0 |
| L-Isoleucine | 0.1 |
| L-Arginine | 0.1 |
| CaCO₃ | 5.0 |

Glucose and magnesium sulfate are sterilized separately. CaCO₃ is dry-heat sterilized at 180° C. for 2 h. The pH is adjusted to 7.0.

Example 10. Production of L-Phenylalanine by E. coli AJ12739ΔpitA

To test the effect of inactivation of the pitA gene on L-phenylalanine production, the DNA fragments from the chromosome of the above-described E. coli MG1655ΔpitA are transferred to the phenylalanine-producing E. coli strain AJ12739 by P1-transduction to obtain strain AJ12739ΔpitA. The strain AJ12739 was deposited in the Russian National Collection of Industrial Microorganisms (VKPM) (Russian Federation, 117545 Moscow, 1$^{st}$ Dorozhny proezd, 1) on Nov. 6, 2001 under the accession number VKPM B-8197 and then converted to a deposit under the Budapest Treaty on Aug. 23, 2002.

E. coli strains AJ12739 and AJ12739ΔpitA are separately cultivated at 37° C. for 18 h in a nutrient broth, and 0.3 mL of the obtained cultures are each inoculated into 3 mL of a fermentation medium in 20×200-mm test tubes and cultivated at 37° C. for 48 h with shaking on a rotary shaker.

After the cultivation, the amount of L-phenylalanine which accumulates in the medium is determined by thin layer chromatography (TLC). The 10×15-cm TLC plates coated with 0.11-mm layers of Sorbfil silica gel containing non-fluorescent indicator (Stock Company Sorbpolymer, Krasnodar, Russian Federation) are used. The Sorbfil plates are developed with a mobile phase consisting of propan-2-ol:ethylacetate:25% aqueous ammonia:water=40:40:7:16 (v/v). A solution of ninhydrin (2%) in acetone is used as a visualizing reagent.

The composition of the fermentation medium (g/L) is as follows:

| | |
|---|---|
| Glucose | 40.0 |
| (NH₄)₂SO₄ | 16.0 |
| K₂HPO₄ | 0.1 |
| MgSO₄•7H₂O | 1.0 |
| FeSO₄•7H₂O | 0.01 |
| MnSO₄•5H₂O | 0.01 |
| Thiamine-HCl | 0.0002 |
| Yeast extract | 2.0 |
| L-Tyrosine | 0.125 |
| CaCO₃ | 20.0 |

Glucose and magnesium sulfate are sterilized separately. CaCO₃ is dry-heat sterilized at 180° C. for 2 h. The pH is adjusted to 7.0.

Example 11. Production of L-Proline by E. coli 702ilvAΔpitA

To test the effect from inactivation of the pitA gene on L-proline production, the DNA fragments from the chromosome of the above-described E. coli MG1655ΔpitA strain are transferred to the proline-producing E. coli strain 702ilvA by P1-transduction to obtain the strain 702ilvAΔpitA. The strain 702ilvA was deposited in the Russian National Collection of Industrial Microorganisms (VKPM) (Russian Federation, 117545 Moscow, 1$^{st}$ Dorozhny proezd, 1) on Jul. 18, 2000 under the accession number VKPM B-8012 and then converted to a deposit under the Budapest Treaty on May 18, 2001.

E. coli strains 702ilvA and 702ilvAΔpitA are separately cultivated for 18-24 h at 37° C. on L-agar plates. Then, these strains are cultivated under the same conditions as in Example 6 (Production of L-glutamic acid).

Example 12. Production of L-Threonine by E. coli B-3996ΔpitA

To test the effect from inactivation of the pitA gene on L-threonine production, the DNA fragments from the chromosome of the above-described E. coli MG1655ΔpitA strain are transferred to the threonine-producing E. coli strain VKPM B-3996 by P1-transduction to obtain the strain B-3996ΔpitA. The strain VKPM B-3996 was deposited on Nov. 19, 1987 in the All-Union Scientific Center of Antibiotics (Russian Federation, 117105 Moscow, Nagatinskaya Street, 3-A) under the accession number RIA 1867. The strain was also deposited in the Russian National Collection of Industrial Microorganisms (VKPM) (Russian Federation, 117545 Moscow, 1$^{st}$ Dorozhny proezd, 1) on Apr. 7, 1987 under the accession number VKPM B-3996.

E. coli strains VKPM B-3996 and B-3996ΔpitA are separately cultivated for 18-24 h at 37° C. on L-agar plates. To obtain a seed culture, the strains are grown on a rotary shaker (250 rpm) at 32° C. for 18 h in 20×200-mm test tubes containing 2 mL of L-broth (Sambrook, J. and Russell, D. W. (2001) "Molecular Cloning: A Laboratory Manual", 3$^{rd}$ ed., Cold Spring Harbor Laboratory Press) supplemented with glucose (4%). Then, the fermentation medium is inoculated with 0.2 mL (10%) of seed material. The fermentation is performed in 2 mL of minimal medium in 20×200-mm test tubes. Cells are grown for 65 h at 32° C. with shaking at 250 rpm.

After the cultivation, the amount of L-threonine which accumulates in the medium is determined by paper chromatography using a mobile phase consisting of butan-1-ol: acetic acid:water=4:1:1 (v/v). A solution of ninhydrin (2%) in acetone is used as a visualizing reagent. A spot containing L-threonine is cut out, L-threonine is eluted with 0.5% water solution of $CdCl_2$, and the amount of L-threonine is estimated spectrophotometrically at 540 nm.

The composition of the fermentation medium (g/L) is as follows:

| | |
|---|---|
| Glucose | 80.0 |
| $(NH_4)_2SO_4$ | 22.0 |
| NaCl | 0.8 |
| $KH_2PO_4$ | 2.0 |
| $MgSO_4 \cdot 7H_2O$ | 0.8 |
| $FeSO_4 \cdot 7H_2O$ | 0.02 |
| $MnSO_4 \cdot 5H_2O$ | 0.02 |
| Thiamine-HCl | 0.0002 |
| Yeast extract | 1.0 |
| $CaCO_3$ | 30.0 |

Glucose and magnesium sulfate are sterilized separately. $CaCO_3$ is sterilized by dry-heat at 180° C. for 2 h. The pH is adjusted to 7.0. The antibiotic is introduced into the medium after sterilization.

Example 13. Production of L-Tryptophan by E. coli SV164(pGH5)ΔpitA

To test the effect from inactivation of the pitA gene on L-tryptophan production, the DNA fragments from the chromosome of the above-described E. coli MG1655ΔpitA strain are transferred to the tryptophan-producing E. coli strain SV164(pGH5) by P1-transduction to obtain the strain SV164(pGH5)ΔpitA. The strain SV164(pGH5) is obtained by introducing the plasmid pGH5 into the E. coli strain SV164. The strain SV164 was obtained from E. coli strain KB862 (DSM7196) and has the trpE allele encoding anthranilate synthase free from feedback inhibition by tryptophan. The plasmid pGH5 harbors a mutant serA gene encoding phosphoglycerate dehydrogenase free from feedback inhibition by serine. The strain SV164(pGH5) was described in detail in U.S. Pat. No. 6,180,373 B1 or EP0662143 B1.

E. coli strains SV164(pGH5) and SV164(pGH5)ΔpitA are separately cultivated with shaking at 37° C. for 18 h in 3 mL of nutrient broth supplemented with tetracycline (20 mg/L, marker of pGH5 plasmid). Then, 0.3 mL of the obtained cultures are each inoculated into 3 mL of a fermentation medium containing tetracycline (20 mg/L) in 20×200-mm test tubes, and cultivated at 37° C. for 48 h with a rotary shaker at 250 rpm.

After the cultivation, the amount of L-tryptophan which accumulates in the medium is determined by TLC. The 10×15-cm TLC plates coated with 0.11-mm layers of Sorbfil silica gel containing non-fluorescent indicator (Stock Company Sorbpolymer, Krasnodar, Russian Federation) are used. The Sorbfil plates are developed with a mobile phase consisting of propan-2-ol:ethylacetate:25% aqueous ammonia:water=40:40:7:16 (v/v). A solution of ninhydrin (2%) in acetone is used as a visualizing reagent. The fermentation medium components are listed in Table 3, but should be sterilized in separate groups (A, B, C, D, E, F, G, and H), as shown, to avoid adverse interactions during sterilization.

TABLE 3

| Solutions | Component | Final concentration, g/L |
|---|---|---|
| A | $KH_2PO_4$ | 1.5 |
| | NaCl | 0.5 |
| | $(NH_4)_2SO_4$ | 1.5 |
| | L-Methionine | 0.05 |
| | L-Phenylalanine | 0.1 |
| | L-Tyrosine | 0.1 |
| | Mameno* (as the amount of nitrogen) | 0.07 |
| B | Glucose | 40.0 |
| | $MgSO_4 \cdot 7H_2O$ | 0.3 |
| C | $CaCl_2$ | 0.011 |
| D | $FeSO_4 \cdot 7H_2O$ | 0.075 |
| | Sodium citrate | 1.0 |
| E | $Na_2MoO_4 \cdot 2H_2O$ | 0.00015 |
| | $H_3BO_3$ | 0.0025 |
| | $CoCl_2 \cdot 6H_2O$ | 0.00007 |
| | $CuSO_4 \cdot 5H_2O$ | 0.00025 |
| | $MnCl_2 \cdot 4H_2O$ | 0.0016 |
| | $ZnSO_4 \cdot 7H_2O$ | 0.0003 |
| F | Thiamine-HCl | 0.005 |
| G | $CaCO_3$ | 30.0 |
| H | Pyridoxine | 0.03 |

The pH of solution A is adjusted to 7.1 with $NH_4OH$.
*Mameno is the soybean meal hydrolysate (Ajinomoto Co., Inc.).

Example 14

Production of L-Valine by E. coli H81ΔpitA Strain

To test the effect from inactivation of the pitA gene on L-valine production, the DNA fragments from the chromosome of the above-described E. coli MG1655ΔpitA strain are transferred to the valine-producing E. coli strain H81 by P1-transduction to obtain the strain H81ΔpitA. The strain H81 was deposited in the Russian National Collection of Industrial Microorganisms (VKPM) (Russian Federation, 117545 Moscow, 1$^{st}$ Dorozhny Proezd, 1) on Jan. 30, 2001 under the accession number VKPM B-8066, and then converted to an international deposit under the Budapest Treaty on Feb. 1, 2002.

E. coli strains H81 and H81ΔpitA are separately cultivated at 37° C. for 18 h in a nutrient broth. The obtained cultures (0.1 mL each) are each inoculated into 2 mL of a fermentation medium in 20×200-mm test tubes, and cultivated at 32° C. for 72 h with a rotary shaker at 250 rpm.

After the cultivation, the amount of L-valine which accumulates in the medium is measured by TLC. The 10×15-cm TLC plates coated with 0.11-mm layers of Sorbfil silica gel containing non-fluorescent indicator (Stock Company Sorbpolymer, Krasnodar, Russian Federation) are used. The Sorbfil plates are developed with a mobile phase consisting of propan-2-ol:ethylacetate:25% aqueous ammonia:water=40:40:7:16 (v/v). A solution of ninhydrin (2%) in acetone is used as a visualizing reagent.

Fermentation Medium Composition (g/L):

| | |
|---|---|
| Glucose | 60.0 |
| $(NH_4)_2SO_4$ | 15.0 |
| $KH_2PO_4$ | 1.5 |
| $MgSO_4 \cdot 7H_2O$ | 1.0 |
| Mameno (TN) | 0.4 |
| $CaCO_3$ | 25.0 |

$CaCo_3$ is dry-heat sterilized at 180° C. for 2 h. The pH is adjusted to 7.0.

While the invention has been described in detail with reference to preferred embodiments thereof, it will be apparent to one skilled in the art that various changes can be made, and equivalents employed, without departing from the scope of the invention. All the cited references herein are incorporated by reference as a part of this application.

INDUSTRIAL APPLICABILITY

According to the present invention, production of L-amino acids such as L-arginine and L-histidine by a bacterium of the family Enterobacteriaceae can be improved.

The invention claimed is:

1. A method for producing an L-amino acid selected from the group consisting of L-His, L-Arg, or combinations thereof, said method comprising:
   (i) cultivating an L-amino acid-producing *Escherichia coli* bacterium in a culture medium to produce and accumulate an L-amino acid in the culture medium or cells of the bacterium, or both; and
   (ii) collecting the L-amino acid from the culture medium or cells of the bacterium, or both,
   wherein said bacterium has been modified to attenuate expression of a phosphate transporter-encoding gene and
   wherein said phosphate transporter-encoding gene is selected from the group consisting of:
   (A) a DNA comprising the nucleotide sequence of SEQ ID NO: 1;
   (B) a DNA comprising the nucleotide sequence of SEQ ID NO: 3;
   (C) a DNA comprising a variant nucleotide sequence of SEQ ID NO: 1 or SEQ ID NO: 3 due to the degeneracy of the genetic code;
   (D) a DNA having an identity of the nucleotide sequence of not less than 75% with respect to the entire nucleotide sequence of SEQ ID NO: 1 or SEQ ID NO: 3, and wherein said nucleotide sequence encodes a protein having inorganic phosphate-transporting activity;
   (E) a DNA encoding a protein comprising the amino acid sequence of SEQ ID NO: 2;
   (F) a DNA encoding a protein comprising the amino acid sequence of SEQ ID NO: 4; and
   (G) a DNA encoding a protein comprising the amino acid sequence of SEQ ID NO: 2 or SEQ ID NO: 4, but wherein said sequence includes substitutions, deletions, insertions, or additions of 1 to 30 amino acid residues, and wherein said protein has inorganic phosphate-transporting activity.

2. The method according to claim 1, wherein said expression of the phosphate transporter-encoding gene is attenuated by inactivation of the phosphate transporter-encoding gene.

3. The method according to claim 2, wherein said phosphate transporter-encoding gene is deleted.

4. The method according to claim 1, wherein said phosphate transporter-encoding gene is pitA or pitB.

* * * * *